United States Patent
Gauthier et al.

(10) Patent No.: US 11,066,470 B2
(45) Date of Patent: Jul. 20, 2021

(54) HUMANIZED ANTIBODIES WITH INCREASED STABILITY

(71) Applicant: INNATE PHARMA, Marseilles (FR)

(72) Inventors: Laurent Gauthier, Marseilles (FR); Nicolas Schneider, Marseilles (FR)

(73) Assignee: INNATE PHARMA, Marseilles (FR)

( * ) Notice: Subject to any disclaimer, the term of this patent is extended or adjusted under 35 U.S.C. 154(b) by 113 days.

(21) Appl. No.: 16/398,472

(22) Filed: Apr. 30, 2019

(65) Prior Publication Data

US 2019/0276536 A1    Sep. 12, 2019

Related U.S. Application Data

(62) Division of application No. 15/125,216, filed as application No. PCT/EP2015/055224 on Mar. 12, 2015, now Pat. No. 10,280,222.

(60) Provisional application No. 61/953,035, filed on Mar. 14, 2014.

(51) Int. Cl.
| | |
|---|---|
| *C07K 16/28* | (2006.01) |
| *C07K 16/30* | (2006.01) |
| *A61K 39/395* | (2006.01) |
| *A61K 47/02* | (2006.01) |
| *A61K 47/12* | (2006.01) |
| *A61K 47/26* | (2006.01) |
| *A61K 39/00* | (2006.01) |
| *A61K 9/00* | (2006.01) |

(52) U.S. Cl.
CPC .... *C07K 16/2803* (2013.01); *A61K 39/39591* (2013.01); *A61K 47/02* (2013.01); *A61K 47/12* (2013.01); *A61K 47/26* (2013.01); *C07K 16/3061* (2013.01); *A61K 9/0019* (2013.01); *A61K 2039/505* (2013.01); *C07K 2317/24* (2013.01); *C07K 2317/52* (2013.01); *C07K 2317/565* (2013.01); *C07K 2317/567* (2013.01); *C07K 2317/71* (2013.01); *C07K 2317/732* (2013.01); *C07K 2317/76* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 6,407,213 B1 | 6/2002 | Carter et al. | |
| 7,399,595 B2 | 7/2008 | Bensussan et al. | |
| 7,919,085 B2 | 4/2011 | Bensussan et al. | |
| 8,268,308 B2 | 9/2012 | Bensussan et al. | |
| 8,518,655 B2 | 8/2013 | Bensussan et al. | |
| 9,181,341 B2 | 11/2015 | Anfossi et al. | |
| 9,828,427 B2 | 11/2017 | Anfossi et al. | |
| 10,174,112 B2 | 1/2019 | Bonnafous et al. | |
| 10,246,510 B2 | 4/2019 | Gauthier et al. | |
| 10,280,222 B2 | 5/2019 | Gauthier et al. | |
| 2015/0232556 A1 | 8/2015 | Gauthier et al. | |
| 2015/0291692 A1 | 10/2015 | Gauthier et al. | |
| 2016/0002345 A1 | 1/2016 | Bonnafous et al. | |
| 2016/0046713 A1 | 2/2016 | Anfossi et al. | |
| 2019/0127463 A1 | 5/2019 | Bonnafous et al. | |
| 2019/0248895 A1 | 8/2019 | Paturel et al. | |

FOREIGN PATENT DOCUMENTS

| | | |
|---|---|---|
| WO | WO 2010/081890 | 7/2010 |
| WO | WO 2014/044686 | 3/2014 |
| WO | WO 2014/128221 | 8/2014 |

OTHER PUBLICATIONS

Igawa, T. et al. "$V_H/V_L$ interface engineering to promote selective expression and inhibit conformational isomerization of thrombopoietin receptor agonist single-chain diabody" *Protein Engineering, Design & Selection*, Jun. 24, 2010, pp. 667-677, vol. 23, No. 8.

McDonagh, C. F. etal. "Improved Yield and Stability of L49-sFv-β-Lactamase, a Single-Chain Antibody Fusion Protein for Anticancer Prodrug Activation, by Protein Engineering" *Bioconjugate Chemistry*, Jul. 25, 2003, pp. 860-869, vol. 14, No. 5.

Wong-Baeza, I. et al. "KIR3DL2 Binds to HLA-B27 Dimers and Free H Chains More Strongly than Other HLA Class I and Promotes the Expansion of T Cells in Ankylosing Spondylitis" *The Journal of Immunology*, Feb. 25, 2013, pp. 3216-3224, vol. 190.

Written Opinion in International Application No. PCT/EP2015/055224, dated May 26, 2015, pp. 1-7.

Klimka, A. et al. "Human anti-CD30 recombinant antibodies by guided phage antibody selection using cell panning" *British Journal of Cancer*, 2000, pp. 252-260, vol. 83.

Masuda, K. et al. "The role of interface framework residues in determining antibody $V_H/V_L$ interaction strength and antigen-binding affinity" *FEBS Journal*, 2006, pp. 2184-2194, vol. 273.

*Primary Examiner* — Amy E Juedes

(74) *Attorney, Agent, or Firm* — Saliwanchik, Lloyd & Eisenschenk

(57) ABSTRACT

The present invention provides antibodies having improved stability. Included are antibodies that are capable of binding to KIR3DL2 polypeptides. The antibodies are suitable for the treatment of disorders characterized by KIR3DL2-expressing cells, particularly CD4+ T cells, including malignancies such as Mycosis Fungoides and Sezary Syndrome, and KIR3DL2-expressing autoimmune disorders.

13 Claims, 2 Drawing Sheets

Specification includes a Sequence Listing.

SEQUENCE LISTING

```
<160> NUMBER OF SEQ ID NOS: 56

<210> SEQ ID NO 1
<211> LENGTH: 434
<212> TYPE: PRT
<213> ORGANISM: HOMO SAPIENS

<400> SEQUENCE: 1

Leu Met Gly Gly Gln Asp Lys Pro Phe Leu Ser Ala Arg Pro Ser Thr
  1               5                  10                  15

Val Val Pro Arg Gly Gly His Val Ala Leu Gln Cys His Tyr Arg Arg
                 20                  25                  30

Gly Phe Asn Asn Phe Met Leu Tyr Lys Glu Asp Arg Ser His Val Pro
             35                  40                  45

Ile Phe His Gly Arg Ile Phe Gln Glu Ser Phe Ile Met Gly Pro Val
         50                  55                  60

Thr Pro Ala His Ala Gly Thr Tyr Arg Cys Arg Gly Ser Arg Pro His
 65                  70                  75                  80

Ser Leu Thr Gly Trp Ser Ala Pro Ser Asn Pro Leu Val Ile Met Val
                 85                  90                  95

Thr Gly Asn His Arg Lys Pro Ser Leu Leu Ala His Pro Gly Pro Leu
            100                 105                 110

Leu Lys Ser Gly Glu Thr Val Ile Leu Gln Cys Trp Ser Asp Val Met
        115                 120                 125

Phe Glu His Phe Phe Leu His Arg Glu Gly Ile Ser Glu Asp Pro Ser
    130                 135                 140

Arg Leu Val Gly Gln Ile His Asp Gly Val Ser Lys Ala Asn Phe Ser
145                 150                 155                 160

Ile Gly Pro Leu Met Pro Val Leu Ala Gly Thr Tyr Arg Cys Tyr Gly
                165                 170                 175

Ser Val Pro His Ser Pro Tyr Gln Leu Ser Ala Pro Ser Asp Pro Leu
            180                 185                 190

Asp Ile Val Ile Thr Gly Leu Tyr Glu Lys Pro Ser Leu Ser Ala Gln
        195                 200                 205

Pro Gly Pro Thr Val Gln Ala Gly Glu Asn Val Thr Leu Ser Cys Ser
    210                 215                 220

Ser Trp Ser Ser Tyr Asp Ile Tyr His Leu Ser Arg Glu Gly Glu Ala
225                 230                 235                 240

His Glu Arg Arg Leu Arg Ala Val Pro Lys Val Asn Arg Thr Phe Gln
                245                 250                 255

Ala Asp Phe Pro Leu Gly Pro Ala Thr His Gly Gly Thr Tyr Arg Cys
            260                 265                 270

Phe Gly Ser Phe Arg Ala Leu Pro Cys Val Trp Ser Asn Ser Ser Asp
        275                 280                 285

Pro Leu Leu Val Ser Val Thr Gly Asn Pro Ser Ser Ser Trp Pro Ser
    290                 295                 300
```

-continued

```
Pro Thr Glu Pro Ser Ser Lys Ser Gly Ile Cys Arg His Leu His Val
305                 310                 315                 320

Leu Ile Gly Thr Ser Val Val Ile Phe Leu Phe Ile Leu Leu Leu Phe
            325                 330                 335

Phe Leu Leu Tyr Arg Trp Cys Ser Asn Lys Lys Asn Ala Ala Val Met
        340                 345                 350

Asp Gln Glu Pro Ala Gly Asp Arg Thr Val Asn Arg Gln Asp Ser Asp
    355                 360                 365

Glu Gln Asp Pro Gln Glu Val Thr Tyr Ala Gln Leu Asp His Cys Val
370                 375                 380

Phe Ile Gln Arg Lys Ile Ser Arg Pro Ser Gln Arg Pro Lys Thr Pro
385                 390                 395                 400

Leu Thr Asp Thr Ser Val Tyr Thr Glu Leu Pro Asn Ala Glu Pro Arg
                405                 410                 415

Ser Lys Val Val Ser Cys Pro Arg Ala Pro Gln Ser Gly Leu Glu Gly
            420                 425                 430

Val Phe
```

<210> SEQ ID NO 2
<211> LENGTH: 5
<212> TYPE: PRT
<213> ORGANISM: MUS MUSCULUS

<400> SEQUENCE: 2

```
Ser Tyr Thr Met His
1               5
```

<210> SEQ ID NO 3
<211> LENGTH: 15
<212> TYPE: PRT
<213> ORGANISM: MUS MUSCULUS

<400> SEQUENCE: 3

```
Tyr Ile Asn Pro Ser Ser Gly Tyr Thr Glu Asn Asn Arg Lys Phe
1               5                   10                  15
```

<210> SEQ ID NO 4
<211> LENGTH: 11
<212> TYPE: PRT
<213> ORGANISM: MUS MUSCULUS

<400> SEQUENCE: 4

```
Leu Gly Lys Gly Leu Leu Pro Pro Phe Asp Tyr
1               5                   10
```

<210> SEQ ID NO 5
<211> LENGTH: 11
<212> TYPE: PRT
<213> ORGANISM: MUS MUSCULUS

<400> SEQUENCE: 5

```
Arg Ala Ser Glu Asn Ile Tyr Ser Asn Leu Ala
1               5                   10
```

<210> SEQ ID NO 6
<211> LENGTH: 7
<212> TYPE: PRT
<213> ORGANISM: MUS MUSCULUS

<400> SEQUENCE: 6

Ala Ala Thr Asn Leu Ala Asp
1               5

<210> SEQ ID NO 7
<211> LENGTH: 9
<212> TYPE: PRT
<213> ORGANISM: MUS MUSCULUS

<400> SEQUENCE: 7

Gln His Phe Trp Gly Thr Pro Tyr Thr
1               5

<210> SEQ ID NO 8
<211> LENGTH: 107
<212> TYPE: PRT
<213> ORGANISM: Artificial
<220> FEATURE:
<223> OTHER INFORMATION: Chimeric human/murine

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Leu
        35                  40                  45

Tyr Ala Ala Thr Asn Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Gly Thr Pro Tyr
                85                  90                  95

Thr Phe Gly Gln Gly Thr Lys Leu Glu Ile Lys
            100                 105

<210> SEQ ID NO 9
<211> LENGTH: 107
<212> TYPE: PRT
<213> ORGANISM: artificial
<220> FEATURE:
<223> OTHER INFORMATION: Chimeric human/mouse

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Gly Thr Pro Tyr
                85                  90                  95

Thr Phe Gly Gly Gly Thr Lys Leu Glu Ile Lys
            100                 105

<210> SEQ ID NO 10
<211> LENGTH: 107

```
<212> TYPE: PRT
<213> ORGANISM: artificial
<220> FEATURE:
<223> OTHER INFORMATION: Chimeric human/mouse

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Thr Leu Thr Ile Ser Ser Leu Gln Pro
65                  70                  75                  80

Glu Asp Phe Ala Thr Tyr Tyr Cys Gln His Phe Trp Gly Thr Pro Tyr
                85                  90                  95

Thr Phe Gly Gly Gly Thr Lys Leu Glu Ile Lys
            100                 105

<210> SEQ ID NO 11
<211> LENGTH: 107
<212> TYPE: PRT
<213> ORGANISM: artificial
<220> FEATURE:
<223> OTHER INFORMATION: Chimeric human/mouse

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Gln Gly Lys Ala Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Thr Leu Thr Ile Asn Ser Leu Gln Pro
65                  70                  75                  80

Glu Asp Phe Ala Thr Tyr Tyr Cys Gln His Phe Trp Gly Thr Pro Tyr
                85                  90                  95

Thr Phe Gly Gly Gly Thr Lys Leu Glu Ile Lys
            100                 105

<210> SEQ ID NO 12
<211> LENGTH: 107
<212> TYPE: PRT
<213> ORGANISM: artificial
<220> FEATURE:
<223> OTHER INFORMATION: Chimeric human/mouse

<400> SEQUENCE: 12

Asp Ile Gln Met Thr Gln Ser Pro Ser Ser Leu Ser Ala Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ala Pro Gln Leu Leu Val
        35                  40                  45

Tyr Ala Ala Thr Asn Leu Ala Asp Gly Val Pro Ser Arg Phe Ser Gly
```

```
            50                  55                  60
Ser Gly Ser Gly Thr Gln Tyr Thr Leu Thr Ile Asn Ser Leu Gln Pro
 65                  70                  75                  80

Glu Asp Phe Ala Thr Tyr Tyr Cys Gln His Phe Trp Gly Thr Pro Tyr
                 85                  90                  95

Thr Phe Gly Gly Gly Thr Lys Leu Glu Ile Lys
            100                 105
```

<210> SEQ ID NO 13
<211> LENGTH: 120
<212> TYPE: PRT
<213> ORGANISM: artificial
<220> FEATURE:
<223> OTHER INFORMATION: Chimeric human/mouse

<400> SEQUENCE: 13

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
                 20                  25                  30

Thr Met His Trp Val Arg Gln Ala Pro Gly Gln Gly Leu Glu Trp Met
             35                  40                  45

Gly Tyr Ile Asn Pro Ser Ser Gly Tyr Thr Glu Asn Asn Arg Lys Phe
 50                  55                  60

Lys Asp Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Leu Gly Lys Gly Leu Leu Pro Pro Phe Asp Tyr Trp Gly Gln
            100                 105                 110

Gly Thr Thr Val Thr Val Ser Ser
        115                 120
```

<210> SEQ ID NO 14
<211> LENGTH: 120
<212> TYPE: PRT
<213> ORGANISM: artificial
<220> FEATURE:
<223> OTHER INFORMATION: Chimeric human/mouse

<400> SEQUENCE: 14

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
                 20                  25                  30

Thr Met His Trp Val Arg Gln Ala Pro Gly Gln Gly Leu Glu Trp Ile
             35                  40                  45

Gly Tyr Ile Asn Pro Ser Ser Gly Tyr Thr Glu Asn Asn Arg Lys Phe
 50                  55                  60

Lys Asp Lys Thr Thr Met Thr Ala Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Leu Gly Lys Gly Leu Leu Pro Pro Phe Asp Tyr Trp Gly Gln
            100                 105                 110

Gly Thr Thr Val Thr Val Ser Ser
        115                 120
```

<210> SEQ ID NO 15
<211> LENGTH: 120
<212> TYPE: PRT
<213> ORGANISM: artificial
<220> FEATURE:
<223> OTHER INFORMATION: Chimeric human/mouse

<400> SEQUENCE: 15

Gln Val Gln Leu Gln Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
                20                  25                  30

Thr Met His Trp Val Arg Gln Ala Pro Gly Gln Gly Leu Glu Trp Ile
            35                  40                  45

Gly Tyr Ile Asn Pro Ser Ser Gly Tyr Thr Glu Asn Asn Arg Lys Phe
        50                  55                  60

Lys Asp Lys Thr Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Gly Lys Gly Leu Leu Pro Pro Phe Asp Tyr Trp Gly Gln
            100                 105                 110

Gly Thr Thr Leu Thr Val Ser Ser
        115                 120

<210> SEQ ID NO 16
<211> LENGTH: 120
<212> TYPE: PRT
<213> ORGANISM: artificial
<220> FEATURE:
<223> OTHER INFORMATION: Chimeric human/mouse

<400> SEQUENCE: 16

Gln Val Gln Leu Val Gln Ser Gly Ala Glu Leu Ala Arg Pro Gly Ala
1               5                   10                  15

Ser Val Lys Val Ser Cys Lys Ala Ser Gly Tyr Thr Phe Thr Ser Tyr
                20                  25                  30

Thr Met His Trp Val Arg Gln Ala Pro Gly Gln Gly Leu Glu Trp Ile
            35                  40                  45

Gly Tyr Ile Asn Pro Ser Ser Gly Tyr Thr Glu Asn Asn Arg Lys Phe
        50                  55                  60

Lys Asp Lys Thr Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Gly Lys Gly Leu Leu Pro Pro Phe Asp Tyr Trp Gly Gln
            100                 105                 110

Gly Thr Thr Val Thr Val Ser Ser
        115                 120

<210> SEQ ID NO 17
<211> LENGTH: 120
<212> TYPE: PRT
<213> ORGANISM: artificial
<220> FEATURE:
<223> OTHER INFORMATION: Chimeric human/mouse

<400> SEQUENCE: 17

Gln Val Gln Leu Gln Gln Ser Gly Ala Glu Val Lys Lys Pro Gly Ala

-continued

```
                1               5                  10                 15
            Ser Val Lys Met Ser Cys Lys Ala Ser Gly Tyr Thr Phe Thr Ser Tyr
                           20                  25                  30

Thr Met His Trp Val Lys Gln Arg Pro Gly Gln Gly Leu Glu Trp Ile
                           35                  40                  45

Gly Tyr Ile Asn Pro Ser Ser Gly Tyr Thr Glu Asn Asn Arg Lys Phe
                           50                  55                  60

Lys Asp Lys Thr Thr Leu Thr Ala Asp Lys Ser Thr Ser Thr Ala Tyr
             65                70                  75                  80

Met Glu Leu Ser Ser Leu Arg Ser Glu Asp Thr Ala Val Tyr Tyr Cys
                           85                  90                  95

Ala Arg Leu Gly Lys Gly Leu Leu Pro Pro Phe Asp Tyr Trp Gly Gln
                          100                 105                 110

Gly Thr Thr Leu Thr Val Ser Ser
                          115                 120
```

<210> SEQ ID NO 18
<211> LENGTH: 5
<212> TYPE: PRT
<213> ORGANISM: mus musculus

<400> SEQUENCE: 18

```
Thr Ala Gly Met Gln
1               5
```

<210> SEQ ID NO 19
<211> LENGTH: 16
<212> TYPE: PRT
<213> ORGANISM: mus musculus

<400> SEQUENCE: 19

```
Trp Ile Asn Ser His Ser Gly Val Pro Lys Tyr Ala Glu Asp Phe Lys
1               5                  10                  15
```

<210> SEQ ID NO 20
<211> LENGTH: 9
<212> TYPE: PRT
<213> ORGANISM: mus musculus

<400> SEQUENCE: 20

```
Gly Gly Asp Glu Gly Val Met Asp Tyr
1               5
```

<210> SEQ ID NO 21
<211> LENGTH: 11
<212> TYPE: PRT
<213> ORGANISM: mus musculus

<400> SEQUENCE: 21

```
Lys Ala Ser Gln Asp Val Ser Thr Ala Val Ala
1               5                  10
```

<210> SEQ ID NO 22
<211> LENGTH: 7
<212> TYPE: PRT
<213> ORGANISM: mus musculus

<400> SEQUENCE: 22

```
Trp Thr Ser Thr Arg His Thr
1               5
```

<210> SEQ ID NO 23
<211> LENGTH: 9
<212> TYPE: PRT
<213> ORGANISM: mus musculus

<400> SEQUENCE: 23

Gln Gln His Tyr Ser Thr Pro Trp Thr
1               5

<210> SEQ ID NO 24
<211> LENGTH: 107
<212> TYPE: PRT
<213> ORGANISM: artificial
<220> FEATURE:
<223> OTHER INFORMATION: Chimeric human/mouse

<400> SEQUENCE: 24

Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Gln Pro Pro Lys Leu Leu Ile
        35                  40                  45

Tyr Trp Thr Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln His Tyr Ser Thr Pro Trp
                85                  90                  95

Thr Phe Gly Gly Gly Thr Lys Val Glu Ile Lys
            100                 105

<210> SEQ ID NO 25
<211> LENGTH: 107
<212> TYPE: PRT
<213> ORGANISM: artificial
<220> FEATURE:
<223> OTHER INFORMATION: Chimeric human/mouse

<400> SEQUENCE: 25

Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Gln Pro Pro Lys Leu Leu Ile
        35                  40                  45

Tyr Trp Thr Ser Thr Arg His Thr Gly Val Pro Asp Arg Phe Ser Gly
    50                  55                  60

Ser Gly Ser Gly Thr Asp Tyr Thr Leu Thr Ile Ser Ser Leu Gln Ala
65                  70                  75                  80

Glu Asp Val Ala Val Tyr Tyr Cys Gln Gln His Tyr Ser Thr Pro Trp
                85                  90                  95

Thr Phe Gly Gly Gly Thr Lys Val Glu Ile Lys
            100                 105

<210> SEQ ID NO 26
<211> LENGTH: 107
<212> TYPE: PRT
<213> ORGANISM: artificial
<220> FEATURE:
<223> OTHER INFORMATION: Chimeric human/mouse

<400> SEQUENCE: 26

Asp Ile Val Met Thr Gln Ser Pro Ser Phe Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Gln Pro Pro Lys Leu Leu Ile
        35                  40                  45

Tyr Trp Thr Ser Thr Arg His Thr Gly Val Pro Asp Arg Phe Ser Gly
    50                  55                  60

Ser Gly Ser Gly Thr Asp Tyr Thr Leu Thr Ile Ser Ser Val Gln Ala
65                  70                  75                  80

Glu Asp Val Ala Val Tyr Tyr Cys Gln Gln His Tyr Ser Thr Pro Trp
                85                  90                  95

Thr Phe Gly Gly Gly Thr Lys Val Glu Ile Lys
            100                 105

<210> SEQ ID NO 27
<211> LENGTH: 107
<212> TYPE: PRT
<213> ORGANISM: artificial
<220> FEATURE:
<223> OTHER INFORMATION: Chimeric human/mouse

<400> SEQUENCE: 27

Asp Ile Val Met Thr Gln Ser Pro Ser Phe Leu Ser Ala Ser Val Gly
1               5                   10                  15

Asp Arg Val Thr Phe Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Trp Thr Ser Thr Arg His Thr Gly Val Pro Asp Arg Phe Ser Gly
    50                  55                  60

Ser Gly Ser Gly Thr Asp Tyr Thr Leu Thr Ile Ser Ser Val Gln Ala
65                  70                  75                  80

Glu Asp Val Ala Val Tyr Tyr Cys Gln Gln His Tyr Ser Thr Pro Trp
                85                  90                  95

Thr Phe Gly Gly Gly Thr Lys Val Glu Ile Lys
            100                 105

<210> SEQ ID NO 28
<211> LENGTH: 107
<212> TYPE: PRT
<213> ORGANISM: artificial
<220> FEATURE:
<223> OTHER INFORMATION: Chimeric human/mouse

<400> SEQUENCE: 28

Asp Ile Val Met Thr Gln Ser His Lys Phe Leu Ser Ala Ser Val Gly
1               5                   10                  15

Asp Arg Val Thr Phe Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Trp Thr Ser Thr Arg His Thr Gly Val Pro Asp Arg Phe Ser Gly
    50                  55                  60

Ser Gly Ser Gly Thr Asp Tyr Thr Leu Thr Ile Ser Ser Val Gln Ala
65                  70                  75                  80

```
Glu Asp Val Ala Val Tyr Tyr Cys Gln Gln His Tyr Ser Thr Pro Trp
                85                  90                  95

Thr Phe Gly Gly Gly Thr Lys Leu Glu Ile Lys
            100                 105

<210> SEQ ID NO 29
<211> LENGTH: 118
<212> TYPE: PRT
<213> ORGANISM: artificial
<220> FEATURE:
<223> OTHER INFORMATION: Chimeric human/mouse

<400> SEQUENCE: 29

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Thr Ala
            20                  25                  30

Gly Met Gln Trp Val Arg Gln Ala Pro Gly Gln Gly Leu Glu Trp Met
        35                  40                  45

Gly Trp Ile Asn Ser His Ser Gly Val Pro Lys Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Gly Gly Asp Glu Gly Val Met Asp Tyr Trp Gly Gln Gly Thr
            100                 105                 110

Thr Val Thr Val Ser Ser
        115

<210> SEQ ID NO 30
<211> LENGTH: 118
<212> TYPE: PRT
<213> ORGANISM: artificial
<220> FEATURE:
<223> OTHER INFORMATION: Chimeric human/mouse

<400> SEQUENCE: 30

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Thr Ala
            20                  25                  30

Gly Met Gln Trp Val Lys Ser Pro Gly Gln Gly Leu Glu Trp Met
        35                  40                  45

Gly Trp Ile Asn Ser His Ser Gly Val Pro Lys Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Gly Gly Asp Glu Gly Val Met Asp Tyr Trp Gly Gln Gly Thr
            100                 105                 110

Thr Val Thr Val Ser Ser
        115

<210> SEQ ID NO 31
<211> LENGTH: 118
<212> TYPE: PRT
```

<213> ORGANISM: artificial
<220> FEATURE:
<223> OTHER INFORMATION: Chimeric human/mouse

<400> SEQUENCE: 31

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Thr Ala
            20                  25                  30

Gly Met Gln Trp Val Arg Gln Ala Pro Gly Gln Gly Leu Glu Trp Ile
        35                  40                  45

Gly Trp Ile Asn Ser His Ser Gly Val Pro Lys Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Gly Gly Asp Glu Gly Val Met Asp Tyr Trp Gly Gln Gly Thr
            100                 105                 110

Thr Val Thr Val Ser Ser
        115

<210> SEQ ID NO 32
<211> LENGTH: 118
<212> TYPE: PRT
<213> ORGANISM: artificial
<220> FEATURE:
<223> OTHER INFORMATION: Chimeric human/mouse

<400> SEQUENCE: 32

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Thr Ala
            20                  25                  30

Gly Met Gln Trp Val Gln Lys Ser Pro Gly Gln Gly Leu Glu Trp Ile
        35                  40                  45

Gly Trp Ile Asn Ser His Ser Gly Val Pro Lys Tyr Ala Glu Asp Phe
    50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Gly Gly Asp Glu Gly Val Met Asp Tyr Trp Gly Gln Gly Thr
            100                 105                 110

Thr Val Thr Val Ser Ser
        115

<210> SEQ ID NO 33
<211> LENGTH: 118
<212> TYPE: PRT
<213> ORGANISM: artificial
<220> FEATURE:
<223> OTHER INFORMATION: Chimeric human/mouse

<400> SEQUENCE: 33

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Thr Ala
            20                  25                  30

Gly Met Gln Trp Val Gln Lys Thr Pro Gly Lys Gly Leu Glu Trp Ile
                35                  40                  45

Gly Trp Ile Asn Ser His Ser Gly Val Pro Lys Tyr Ala Glu Asp Phe
        50                  55                  60

Lys Gly Arg Phe Ala Phe Ser Leu Asp Thr Ser Ala Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Gly Gly Asp Glu Gly Val Met Asp Tyr Trp Gly Gln Gly Thr
                100                 105                 110

Ser Val Thr Val Ser Ser
        115

<210> SEQ ID NO 34
<211> LENGTH: 107
<212> TYPE: PRT
<213> ORGANISM: mus musculus

<400> SEQUENCE: 34

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Tyr
                85                  90                  95

Thr Phe Gly Gly Gly Thr Lys Leu Glu Ile Lys
                100                 105

<210> SEQ ID NO 35
<211> LENGTH: 88
<212> TYPE: PRT
<213> ORGANISM: homo sapiens

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Ser
            20                  25                  30

Leu Ala Trp Tyr Gln Gln Lys Pro Gly Lys Ala Pro Lys Leu Leu Leu
        35                  40                  45

Tyr Ala Ala Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys
                85

<210> SEQ ID NO 36
<211> LENGTH: 107
<212> TYPE: PRT
<213> ORGANISM: artificial

<220> FEATURE:
<223> OTHER INFORMATION: Chimeric human/mouse

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105

<210> SEQ ID NO 37
<211> LENGTH: 107
<212> TYPE: PRT
<213> ORGANISM: mus musculus

<400> SEQUENCE: 37

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Ile Ile Tyr Ser Asn
            20                  25                  30

Leu Ala Trp Tyr Gln Gln Lys Gln Gly Lys Ser Pro Gln Leu Leu Val
        35                  40                  45

Tyr Ser Ala Thr Asn Leu Ala Glu Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Asn Pro Trp
                85                  90                  95

Thr Phe Gly Gly Gly Thr Lys Leu Glu Ile Lys
            100                 105

<210> SEQ ID NO 38
<211> LENGTH: 120
<212> TYPE: PRT
<213> ORGANISM: mus musculus

<400> SEQUENCE: 38

Gln Val Gln Leu Gln Gln Ser Ala Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Ile Asn Pro Ser Ser Gly Tyr Thr Glu Asn Asn Arg Lys Phe
    50                  55                  60

Lys Asp Lys Thr Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys

```
                    85                  90                  95

Ala Arg Leu Gly Lys Gly Leu Leu Pro Pro Phe Asp Tyr Trp Gly Gln
            100                 105                 110

Gly Thr Thr Leu Thr Val Ser Ser
        115                 120

<210> SEQ ID NO 39
<211> LENGTH: 98
<212> TYPE: PRT
<213> ORGANISM: homo sapiens

<400> SEQUENCE: 39

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 40
<211> LENGTH: 118
<212> TYPE: PRT
<213> ORGANISM: artificial
<220> FEATURE:
<223> OTHER INFORMATION: Chimeric human/mouse

<400> SEQUENCE: 40

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Ser Tyr
            20                  25                  30

Tyr Met Tyr Trp Val Lys Gln Ala Pro Gly Gln Gly Leu Glu Trp Ile
        35                  40                  45

Gly Glu Ile Asn Pro Ser Asn Gly Asp Thr Asn Phe Asn Glu Lys Phe
    50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
            100                 105                 110

Leu Val Thr Val Ser Ser
        115

<210> SEQ ID NO 41
<211> LENGTH: 118
<212> TYPE: PRT
<213> ORGANISM: artificial
<220> FEATURE:
<223> OTHER INFORMATION: Chimeric human/mouse

<400> SEQUENCE: 41
```

```
Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Ser Tyr
            20                  25                  30

Trp Met Gln Trp Val Lys Gln Ala Pro Gly Gln Gly Leu Glu Trp Met
            35                  40                  45

Gly Glu Ile Asp Pro Ser Asp Ser Tyr Thr Asn Tyr Asn Gln Lys Phe
        50                  55                  60

Lys Gly Lys Ala Thr Leu Thr Val Asp Thr Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Arg Asp Tyr Trp Tyr Phe Asp Val Trp Gly Gly Thr
            100                 105                 110

Leu Val Thr Val Ser Ser
            115

<210> SEQ ID NO 42
<211> LENGTH: 120
<212> TYPE: PRT
<213> ORGANISM: mus musculus

<400> SEQUENCE: 42

Glu Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
            35                  40                  45

Gly Tyr Ile Asn Pro Ser Ser Gly Tyr Ser Asn Tyr Asn Gln Lys Phe
        50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ser Arg Pro Val Val Arg Leu Gly Tyr Asn Phe Asp Tyr Trp Gly Gln
            100                 105                 110

Gly Ser Thr Leu Thr Val Ser Ser
            115                 120

<210> SEQ ID NO 43
<211> LENGTH: 107
<212> TYPE: PRT
<213> ORGANISM: mus musculus

<400> SEQUENCE: 43

Asp Ile Val Met Thr Gln Ser His Lys Phe Met Ser Thr Ser Leu Gly
1               5                   10                  15

Asp Arg Val Ser Phe Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
            35                  40                  45

Tyr Trp Thr Ser Thr Arg His Thr Gly Val Pro Asp Arg Phe Thr Gly
        50                  55                  60

Ser Gly Ser Gly Thr Asp Tyr Thr Leu Thr Ile Ser Ser Val Gln Ala
65                  70                  75                  80
```

```
Glu Asp Leu Ala Leu Tyr Tyr Cys Gln Gln His Tyr Ser Thr Pro Trp
                85                  90                  95

Thr Phe Gly Gly Gly Thr Lys Leu Glu Ile Lys
            100                 105

<210> SEQ ID NO 44
<211> LENGTH: 88
<212> TYPE: PRT
<213> ORGANISM: homo sapiens

<400> SEQUENCE: 44

Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys
                85

<210> SEQ ID NO 45
<211> LENGTH: 86
<212> TYPE: PRT
<213> ORGANISM: homo sapiens

<400> SEQUENCE: 45

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Leu Ala
            20                  25                  30

Trp Tyr Gln Gln Lys Pro Gly Gln Pro Pro Lys Leu Leu Ile Tyr Trp
        35                  40                  45

Ala Ser Thr Arg Glu Ser Gly Val Pro Asp Arg Phe Ser Gly Ser Gly
    50                  55                  60

Ser Gly Thr Asp Phe Thr Leu Thr Ile Ser Ser Leu Gln Ala Glu Asp
65                  70                  75                  80

Val Ala Val Tyr Tyr Cys
                85

<210> SEQ ID NO 46
<211> LENGTH: 107
<212> TYPE: PRT
<213> ORGANISM: mus musculus

<400> SEQUENCE: 46

Asp Ile Val Met Thr Gln Ser Pro Lys Phe Met Ser Thr Ser Val Gly
1               5                   10                  15

Asp Arg Val Thr Ile Thr Cys Lys Ala Ser Gln Asp Val Ser Thr Ala
            20                  25                  30

Val Val Trp Tyr Gln Gln Lys Pro Gly Gln Ser Pro Lys Leu Leu Ile
        35                  40                  45

Tyr Trp Ala Ser Thr Arg His Ile Gly Val Pro Asp Arg Phe Ala Gly
    50                  55                  60
```

```
Ser Gly Ser Gly Thr Asp Tyr Thr Leu Thr Ile Ser Ser Val Gln Ala
 65                  70                  75                  80

Glu Asp Leu Ala Leu Tyr Tyr Cys Gln Gln His Tyr Ser Pro Pro Trp
                 85                  90                  95

Thr Phe Gly Gly Gly Thr Lys Leu Glu Ile Lys
                100                 105
```

<210> SEQ ID NO 47
<211> LENGTH: 106
<212> TYPE: PRT
<213> ORGANISM: artificial
<220> FEATURE:
<223> OTHER INFORMATION: Chimeric human/mouse

<400> SEQUENCE: 47

```
Asp Ile Val Met Ser Gln Ser Pro Asp Ser Leu Ala Val Ser Leu Gly
  1               5                  10                  15

Glu Arg Val Thr Leu Asn Cys Lys Ser Ser Gln Ser Leu Leu Tyr Leu
                 20                  25                  30

Ala Trp Tyr Gln Gln Lys Pro Gly Gln Ser Pro Lys Leu Leu Ile Tyr
             35                  40                  45

Trp Ala Ser Ala Arg Glu Ser Gly Val Pro Asp Arg Phe Ser Gly Ser
 50                  55                  60

Gly Ser Gly Thr Asp Phe Thr Leu Thr Ile Ser Ser Val Gln Ala Glu
 65                  70                  75                  80

Asp Val Ala Val Tyr Tyr Cys Gln Gln Tyr Tyr Ser Tyr Pro Leu Thr
                 85                  90                  95

Phe Gly Ala Gly Thr Lys Leu Glu Leu Lys
                100                 105
```

<210> SEQ ID NO 48
<211> LENGTH: 107
<212> TYPE: PRT
<213> ORGANISM: artificial
<220> FEATURE:
<223> OTHER INFORMATION: Chimeric human/mouse

<400> SEQUENCE: 48

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Arg Asp Ile Lys Ser Tyr
                 20                  25                  30

Leu Asn Trp Tyr Gln Gln Lys Pro Gly Lys Ala Pro Lys Val Leu Ile
             35                  40                  45

Tyr Tyr Ala Thr Ser Leu Ala Glu Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Leu Gln His Gly Glu Ser Pro Trp
                 85                  90                  95

Thr Phe Gly Gln Gly Thr Lys Val Glu Ile Lys
                100                 105
```

<210> SEQ ID NO 49
<211> LENGTH: 107
<212> TYPE: PRT
<213> ORGANISM: artificial
<220> FEATURE:
<223> OTHER INFORMATION: Chimeric human/mouse

```
<400> SEQUENCE: 49

Asp Ile Gln Met Thr Gln Ser Pro Ser Thr Leu Ser Ala Ser Val Gly
1               5                   10                  15

Asp Arg Val Thr Ile Thr Cys Lys Ala Ser Glu Asn Val Asp Thr Tyr
            20                  25                  30

Val Ser Trp Tyr Gln Gln Lys Pro Gly Lys Ala Pro Lys Leu Leu Ile
        35                  40                  45

Tyr Gly Ala Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gly Gln Ser Tyr Asn Tyr Pro Phe
                85                  90                  95

Thr Phe Gly Gln Gly Thr Lys Val Glu Val Lys
            100                 105

<210> SEQ ID NO 50
<211> LENGTH: 107
<212> TYPE: PRT
<213> ORGANISM: artificial
<220> FEATURE:
<223> OTHER INFORMATION: Chimeric human/mouse

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Glu Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 51
<211> LENGTH: 107
<212> TYPE: PRT
<213> ORGANISM: artificial
<220> FEATURE:
<223> OTHER INFORMATION: Chimeric human/mouse

<400> SEQUENCE: 51

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Thr Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80
```

```
Glu Asp Phe Ala Thr Tyr Tyr Cys Gln Gln Gly Asn Thr Leu Pro Pro
                85                  90                  95

Thr Phe Gly Gln Gly Thr Lys Val Glu Ile Lys
        100                 105
```

<210> SEQ ID NO 52
<211> LENGTH: 118
<212> TYPE: PRT
<213> ORGANISM: mus musculus

<400> SEQUENCE: 52

```
Gln Ile Gln Leu Val Gln Ser Gly Pro Glu Leu Lys Lys Pro Gly Glu
1               5                   10                  15

Thr Val Arg Ile Ser Cys Lys Ala Ser Gly Tyr Thr Phe Thr Thr Ala
            20                  25                  30

Gly Met Gln Trp Val Gln Lys Thr Pro Gly Lys Gly Leu Lys Trp Ile
        35                  40                  45

Gly Trp Ile Asn Ser His Ser Gly Val Pro Lys Tyr Ala Glu Asp Phe
    50                  55                  60

Lys Gly Arg Phe Ala Phe Ser Leu Glu Thr Ser Ala Ser Thr Ala Tyr
65                  70                  75                  80

Leu Gln Ile Ser Thr Leu Lys Asn Glu Asp Thr Ala Thr Tyr Phe Cys
                85                  90                  95

Ala Arg Gly Gly Asp Glu Gly Val Met Asp Tyr Trp Gly Gln Gly Thr
            100                 105                 110

Ser Val Thr Val Ser Ser
        115
```

<210> SEQ ID NO 53
<211> LENGTH: 98
<212> TYPE: PRT
<213> ORGANISM: homo sapiens

<400> SEQUENCE: 53

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg
```

<210> SEQ ID NO 54
<211> LENGTH: 95
<212> TYPE: PRT
<213> ORGANISM: homo sapiens

<400> SEQUENCE: 54

```
Gln Val Gln Leu Val Gln Ser Trp Ala Glu Val Arg Lys Ser Gly Ala
1               5                   10                  15

Ser Val Lys Val Ser Cys Ser Phe Ser Gly Phe Thr Ile Thr Ser Tyr
            20                  25                  30
```

```
Gly Ile His Trp Val Gln Ser Pro Gly Gln Gly Leu Glu Trp Met
            35                  40                  45

Gly Trp Ile Asn Pro Asn Gly Ser Pro Ser Tyr Ala Lys Lys Phe
    50                  55                  60

Gln Gly Arg Phe Thr Met Thr Arg Asp Met Ser Thr Thr Ala Tyr
65                  70                  75                  80

Thr Asp Leu Ser Ser Leu Thr Ser Glu Asp Met Ala Val Tyr Tyr
                85                  90                  95

<210> SEQ ID NO 55
<211> LENGTH: 117
<212> TYPE: PRT
<213> ORGANISM: artificial
<220> FEATURE:
<223> OTHER INFORMATION: Chimeric human/mouse

<400> SEQUENCE: 55

Glu Val Gln Leu Val Glu Ser Gly Gly Gly Leu Val Gln Pro Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
            35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Trp Tyr Phe Asp Val Trp Gly Gln Gly Thr Leu
            100                 105                 110

Val Thr Val Ser Ser
        115

<210> SEQ ID NO 56
<211> LENGTH: 116
<212> TYPE: PRT
<213> ORGANISM: artificial
<220> FEATURE:
<223> OTHER INFORMATION: Chimeric human/mouse

<400> SEQUENCE: 56

Glu Val Gln Leu Val Gln Ser Gly Pro Gly Leu Val Gln Pro Gly Gly
1               5                   10                  15

Ser Val Arg Ile Ser Cys Ala Ala Ser Gly Tyr Thr Phe Thr Asn Tyr
            20                  25                  30

Gly Met Asn Trp Val Lys Gln Ala Pro Gly Lys Gly Leu Glu Trp Met
            35                  40                  45

Gly Trp Ile Asn Thr Tyr Thr Gly Glu Ser Thr Tyr Ala Asp Ser Phe
    50                  55                  60

Lys Gly Arg Phe Thr Phe Ser Leu Asp Thr Ser Ala Ser Ala Ala Tyr
65                  70                  75                  80
```

```
Leu Gln Ile Asn Ser Leu Arg Ala Glu Asp Thr Ala Val Tyr Tyr Cys
                85                  90                  95

Ala Arg Phe Ala Ile Lys Gly Asp Tyr Trp Gly Gln Gly Thr Leu Leu
            100                 105                 110

Thr Val Ser Ser
        115
```

HUMANIZED ANTIBODIES WITH INCREASED STABILITY

FIELD OF THE INVENTION

The present invention provides antibodies having improved stability. Included are antibodies that are capable of binding to KIR3DL2 polypeptides. The antibodies are suitable for the treatment of disorders characterized by KIR3DL2-expressing cells, particularly CD4+ T cells, including malignancies such as Mycosis Fungoides and Sezary Syndrome, and KIR3DL2-expressing autoimmune disorders.

CROSS-REFERENCE TO RELATED APPLICATIONS

This application is a divisional of U.S. Ser. No. 15/125,216, filed Sep. 12, 2016, now U.S. Pat. No. 10,280,222, which is the U.S. national stage application of International Patent Application No. PCT/EP2015/055224, filed Mar. 12, 2015, which claims the benefit of U.S. Provisional Application Ser. No. 61/953,035, filed Mar. 14, 2014, the disclosures of which are hereby incorporated by reference in their entirety, including all figures, tables and amino acid or nucleic acid sequences.

REFERENCE TO SEQUENCE LISTING

The present application is being filed along with a Sequence Listing in electronic format. The Sequence Listing is provided as a file entitled "Seq-List", created 11 Mar. 2015, which is 49 KB in size. The information in the electronic format of the Sequence Listing is incorporated herein by reference in its entirety.

BACKGROUND

Killer immunoglobulin-like receptors (KIR) are a family of receptors that, along with C-type lectin receptors (CD94-NKG2), are used by human NK cells and T-lymphocyte subsets to specifically recognize MEW class I molecules. Certain inhibitory and activating KIR have highly similar extracellular domains and are recognized by the same monoclonal antibody, e.g. KIR2DL1 and KIR2DS1 are both recognized by EB6, and 2DL2 and 2DS2 by GL183. Three criteria (number of extracellular Ig-like domains (domains D0, D1, D2), cytoplasmic tail length, and sequence analogy) have been used to categorize the KIR proteins into 13 groups, namely KIR3DL1-2, KIR3DS1, KIR2DL1-5, and KIR2DS1-5. The nomenclature 2D for 2 domains or 3D for 3 domains give the number of Ig-like domains; receptors with either long or short cytoplasmic domains are further classified as L or S. (Pascal V. et al., 2007 J. Immunol. 179:1625-1633) The inhibitory receptors possess long (L) cytoplasmic tails (i.e., KIR2DL or KIR3DL) containing a canonical ITIM that becomes tyrosine phosphorylated upon KIR engagement of their HLA class I ligands. The phosphorylated ITIM recruits the Src homology 2 domain containing protein tyrosine phosphatases Src homology 2 domain-containing phosphatase 1 and/or Src homology 2 domain-containing phosphatase 2, which dephosphorylate cellular substrates, thus aborting the NK activation signal, i.e., sparing target cells with appropriate self-MHC class I expression. Receptors with short (S) cytoplasmic tails lack ITIMs (i.e., KIR2DS or KIR3DS). These activating KIR contain a charged residue within their transmembrane domain facilitating interaction with the signaling chain KARAP/DAP12. Engagement of the KIR2DS family of receptors has been shown to lead to a cascade of KARAP/DAP12-mediated signaling events culminating in increased NK cell cytolytic activity and the production of proinflammatory cytokines such as IFN-γ (Pascal et al. 2007 J. Immunol. 179: 1625-1633). Mature NK cells are predicted to acquire at least one inhibitory receptor specific for a self-MHC class I molecule, which generally functionally prevails over potentially auto-reactive activating molecules. It is proposed that the response of NK cells represents the integrated outcome of both activating and inhibitory signaling by KIR and other receptors.

KIR3DL2 has been studied as a target for the treatment of malignancies involving CD4+ T cells that express KIR3DL2 receptors, particularly CD4+ T cells, including malignancies such as Mycosis Fungoides and Sezary Syndrome (see, e.g. PCT publications WO2010/081890 and WO02/50122). A ligand of KIR3DL2, HLA-B27, is strongly associated with the Spondyloarthritides (SpA) a group of debilitating inflammatory arthritic disorders typified by Ankylosing Spondylitis (AS). KIR3DL2 ligation by B27 dimers promotes the survival of Th17 and NK cell subsets (Bowness, et al. (2011) *Journal of immunology* 186:2672-2680; Chan, et al. (2005) *Arthritis Rheum* 52:3586-3595). It has been shown that that there are increased proportions of pathogenic Th17 and NK cell subsets expressing KIR3DL2 in patients with SpA. Studies strongly suggest that KIR3DL2-B27 interactions have a central role to play in SpA and that KIR3DL2 is a promising therapeutic target.

The existence of antibodies reactive against various KIR3D polypeptides have been reported. The existence of two anti-KIR3DL2 antibodies have been reported: Q241 and Q66 (Pende, et al. (1996) J Exp Med 184:505-518). However, these two antibodies are of the IgM isotype (pentamers) and are not readily suited to pharmaceutical use; furthermore, if their variable regions were placed in the context of a bivalent IgG type antibody, their affinity would be expected to be low. Cells referred to as "AZ158" producing a further antibody was reported (Parolini, S., et al. (2002) In Leucocyte typing VII. D. Mason, editor. Oxford University Press, Oxford. 415-417; PCT publication WO2010/081890). Antibody 5.133 is available from Miltenty Biotech (Auburn Calif.). Both antibodies AZ158 and 5.133 bind KIR3DL2 as well as KIR3DL1 (and further the highly homologous KIR3DS1). KIR3DL2 and KIR3DL1 share relatively high amino acid identity and various HLA ligands that bind KIR3DL2 are also recognized by KIR3DL1. Despite immunizations that gave rise to AZ158, Q241 and Q66, there is a need for improved antibodies in therapeutic and other applications.

SUMMARY OF THE INVENTION

In one aspect, provided are anti-KIR3DL2 antibodies with human frameworks that both have high affinity antigen binding and stability in pharmaceutical formulations. The inventors developed antibodies with different single-gene and mosaic human frameworks and discovered that certain amino acids at residue 39 in the heavy chain and 38 in the light chain (Abnum) provide strongly increased physical stability.

The exemplary antibodies have been developed using antigen combining regions of antibodies 2B12 and 10G5. Antibodies 2B12 and 10G5 CDRs are described in PCT application number PCT/EP2013/069302 filed 17 Sep. 2013. Anti-KIR3DL2 mAbs 2B12 and 10G5 have the advantageous property of not binding the closely related (by homology) KIR3DL1, nor causing KIR3DL2 internalization. KIR3DL2 internalization strongly hampers ADCC-based approaches. The antibodies are capable of mediating ADCC when of appropriate isotype (e.g. IgG1), but are also capable of inhibiting KIR3DL2-HLA B27 dimer interactions with KIR3DL2. Notably, ligand blockade can be achieved without causing receptor internalization. Antibodies that block one or more natural ligands of KIR3DL2 are thus well-suited for treating or preventing inflammatory disorders, either as a depleting or non-depleting mAb format. The epitopes on KIR3DL2 bound by the antibodies have been determined, as both antibodies 10G5 and 2B12 lost binding to KIR3DL2 mutants that have substitutions at residues I60 and G62. Antibody 10G5 further loses binding to KIR3DL2 mutants that have substitutions at includes residues P14, S15 and H23, and at residues R13, A25 and Q27. The antibodies compete with each other for binding to KIR3DL2 polypeptides in native configuration as expressed on the surface of cells.

In one embodiment, the invention provides a humanized 2B12 or 10G5 antibody. In one embodiment, the invention provides a humanized 2B12 or 10G5 antibody having a mosaic human framework in a light chain and/or heavy chain. Exemplary complementarity-determining region (CDR) residues or sequences and/or sites for amino acid substitutions in framework region (FR) of such humanized antibodies having improved properties such as, e.g., lower immunogenicity, improved antigen-binding or other functional properties, and/or improved physicochemical properties such as, e.g., better stability, are provided. In one embodiment, the human framework sequence comprises a back-mutation.

The framework and variable regions provided herein confer onto 2B12 and 10G5 high physical stability and low aggregation propensity under conditions found in pharmaceutical formulations. In particular, provided are antibodies having the antigen combining regions of 2B12 or 10G5, with substantial human framework regions, wherein the antibody comprises in its heavy chain a glutamine (Q) at position 39 and in its light chain a glutamine at position 38 (Abnum numbering). Without wishing to be bound by theory, it is believed that when a glutamine is present in the light chain at residue 38 (Abnum numbering) H-bonds are built between VH_Q39 and VL_Q38 (see FIG. 1), resulting in greater physical stability of the antibody. These two H-bonds may stabilise the quaternary structure of the mAb, preventing the exposition of hydrophobic portions that are responsible for protein aggregation.

In one embodiment, the antibody has human VH and VL acceptor frameworks, wherein the antibody comprises in its heavy chain a glutamine residue at residue 39 and in its light chain a glutamine at residue 38. A VH and/or VL human acceptor framework may comprise a back-mutation (e.g. one, two, three or four or more amino acid substitutions to the corresponding donor residue in one or more of the framework regions) compared to a naturally occurring human acceptor framework. Optionally the antibody binds to the same epitope as antibodies 2B12 or 10G5.

In one embodiment, the antibody comprises heavy chain frameworks 1 (FW1) and 2 (FW2) derived from the human VH7 subgroup. Optionally, the antibody comprises heavy chain framework 3 (FW3) derived from the human VH7 subgroup. Optionally, the antibody comprises heavy chain framework 4 (FW4) is derived from a JH6 subgroup. In one embodiment, the antibody comprises light chain acceptor frameworks of VK1 and/or VK4 subgroup, optionally combined with a JK4 subgroup. Optionally, the antibody comprises light chain FW1 derived from the human VK1 subgroup, and light chain FW2 and light chain FW3 derived from the human VK4 subgroup. Optionally, the antibody comprises light chain FW4 derived from a JK4 subgroup.

In one embodiment, provided is an isolated monoclonal antibody that binds KIR3DL2 comprising a heavy chain comprising the heavy chain CDR1, 2 and 3 of antibody 2B12 and a human heavy chain acceptor framework of human VH7 subgroup, optionally combined with a JH6 subgroup, and a light chain comprising the light chain CDR1, 2 and 3 of antibody 2B12 a human light chain acceptor framework of VK1 and/or VK4 subgroup, optionally combined with a JK4 subgroup. In one embodiment, the heavy chain frameworks comprise one or more back-mutations. In one embodiment, the light chain frameworks comprise one or more back-mutations. In one embodiment, the heavy chain frameworks comprise (collectively) one, two or three back-mutations. In one embodiment, the light chain frameworks comprise (collectively) one or two back-mutations.

In one embodiment, the antibody comprises a heavy chain comprising the heavy chain CDR1, 2 and 3 of antibody 2B12 and a human heavy chain acceptor framework, wherein frameworks 1 (FW1) and 2 (FW2) are derived from the human VH7 subgroup. Optionally, framework 3 (FW3) is derived from the human VH7 subgroup. Optionally, framework 4 (FW4) is derived from a JH6 subgroup. Optionally, the antibody comprises a light chain comprising the light chain CDR1, 2 and 3 of antibody 2B12 and a human light chain acceptor framework of VK1 and/or VK4 subgroup, optionally combined with a JK4 subgroup. Optionally, light chain FW1 is derived from the human VK1 subgroup and light chain FW2 and light chain FW3 are derived from the human VK4 subgroup. Optionally, light chain FW4 is derived from a JK4 subgroup. In one embodiment, the heavy chain frameworks comprise one or more back-mutations. In one embodiment, the light chain frameworks comprise one or more back-mutations. In one embodiment, the heavy chain frameworks comprise (collectively) one, two or three back-mutations. In one embodiment, the light chain frameworks comprise (collectively) one or two back-mutations.

In one embodiment, the VH7 subgroup gene is IGHV7-4 (e.g. IGHV7-4-1*02, a gene encoding the amino acid sequence shown in SEQ ID NO: 53). In one embodiment, the VK1 subgroup gene is IGKV1-39, e.g., a gene encoding the amino acid sequence shown in SEQ ID NO: 44. In one embodiment, the VK4 subgroup gene is IGKV4-1, e.g., a gene encoding the amino acid sequence shown in SEQ ID NO: 45.

In one embodiment, provided is an isolated monoclonal antibody that binds KIR3DL2 comprising a heavy chain comprising the heavy chain CDR1, 2 and 3 of antibody 10G5 and a human heavy chain acceptor framework derived from human VH1 subgroup (e.g. IGHV1-46), and a light chain comprising the light chain CDR1, 2 and 3 of antibody 10G5 and a human light chain acceptor framework derived from the VK1 subgroup (e.g. IGKV1-NL1). In one embodiment, the heavy chain frameworks comprise one or more back-mutations. In one embodiment, the light chain frameworks comprise one or more back-mutations.

In one embodiment, the antibody comprises has a human heavy chain acceptor framework of VH1 and/or VH7 subgroup combined with a JH6 subgroup, and a human light chain acceptor framework of VK1 and/or VK4 subgroup combined with a JK4 subgroup.

In another aspect, the invention provides an isolated humanized antibody that binds a human KIR3DL2 polypeptide and comprises a CDR-L1, a CDR-L2, a CDR-L3, a CDR-H1, a CDR-H2 and a CDR-H3; a glutamine (Q) residue at position 39 of the VH domain and a glutamine at position 38 of the VL domain. The glutamine (Q) residue at position 39 may exist naturally in the human VH framework sequence, or may be introduced by amino acid substitution or other modification of the sequence.

In one embodiment, provided is a humanized antibody comprising the heavy and light chain CDR1, 2 and 3 of antibody 2B12 or 10G5. In one embodiment, provided is an antibody comprising a human acceptor framework that binds a KIR3DL2 polypeptide without substantially binding to a KIR3DL1 polypeptide, wherein the antibody comprises the heavy and light chain CDR1, 2 and 3 of antibody 2B12 or 10G5, wherein one or more of the human framework regions comprise an amino acid substitution. Optionally, the substitution is a back mutation. Optionally, the substitution is a substitution disclosed herein. Optionally, the antibody comprises in its heavy chain a glutamine at residue 39 and in its light chain a glutamine at residue 38.

In one aspect, provided is a humanized 2B12 monoclonal antibody comprising:
(a) a heavy chain CDR 1, 2 and 3 (HCDR1, HCDR2, HCDR3) comprising a sequence of SEQ ID NOS: 18 (HCDR1), SEQ ID NOS: 19 (HCDR2) and SEQ ID NO: 20 (HCDR3) respectively, and (b) a light chain CDR 1, 2 and 3 (LCDR1, LCDR2, LCDR3) comprising a sequence of SEQ ID NO: 21, 22 and 23, respectively. Optionally, the antibody has a human heavy chain acceptor framework of VH1 and/or VH7 subgroup combined with a JH6 subgroup, and a human light chain acceptor framework of VK1 and/or VK4 subgroup combined with a JK4 subgroup. Optionally, the human light and/or heavy chain acceptor frameworks comprise a substitution (e.g. a back-mutation).

Optionally, in any embodiments herein of a 2B12 antibody, the heavy chain framework may have one or more substitutions at position(s) selected from the group consisting of: residues 2, 38, 39, 40, 43, 48, 68, 72c, 9 and 108 (Abnum numbering), including any combinations thereof. Optionally, in any embodiments herein of a 2B12 antibody, the light chain framework has one or more substitutions at position(s) selected from the group consisting of: residues 3, 8, 9, 21, 43, 71, 78 and 104 (Abnum numbering), including any combinations thereof. In one embodiment, a substitution(s) is a back mutation.

In one embodiment, provided is a humanized 2B12 monoclonal antibody comprising:
(a) a heavy chain variable region comprising an amino acid sequence selected from the group consisting of 2B12-H0, -H1, -H2, -H3 and -H4; and
(b) a light chain variable region comprising an amino acid sequence selected from the group consisting of 2B12-L0, -L1, -L2, -L3 and -L4.

In one embodiment, provided is a humanized 2B12 monoclonal antibody comprising:
(a) a heavy chain variable region comprising an amino acid sequence selected from the group consisting of SEQ ID NOS: 29-33, and
(b) a light chain variable region comprising an amino acid sequence selected from the group consisting of SEQ ID NOS: 24-28.

In one embodiment, provided is a humanized 2B12 monoclonal antibody comprising:
(a) a heavy chain variable region comprising an amino acid sequence of SEQ ID N: 29, and
(b) a light chain variable region comprising an amino acid sequence of SEQ ID N: 24.

In one embodiment, provided is a humanized 2B12 monoclonal antibody comprising:
(a) a heavy chain variable region comprising an amino acid sequence of SEQ ID N: 31, and
(b) a light chain variable region comprising an amino acid sequence of SEQ ID NO: 25.

In one embodiment, provided is a humanized 2B12 monoclonal antibody comprising:
(a) a heavy chain variable region comprising an amino acid sequence of SEQ ID NO: 31, and
(b) a light chain variable region comprising an amino acid sequence of SEQ ID NO: 26.

In one embodiment, provided is a humanized 2B12 monoclonal antibody comprising:
(a) a heavy chain variable region comprising an amino acid sequence of SEQ ID NO: 32, and
(b) a light chain variable region comprising an amino acid sequence of SEQ ID NO: 26.

In one embodiment, provided is a humanized 2B12 monoclonal antibody comprising:
(a) a heavy chain variable region comprising an amino acid sequence of SEQ ID NO: 33, and
(b) a light chain variable region comprising an amino acid sequence of SEQ ID NO: 26.

In one embodiment, a heavy chain variable region comprises one or more back-mutations in one, two, three or four of its framework regions. In one embodiment, a light chain variable region comprises one or more back-mutations in one, two, three or four of its framework regions.

In one aspect, provided is a pharmaceutically acceptable and active formulation comprising (a) about 0.05 mg/mL to about 10 mg/mL of an IgG antibody molecule comprising a heavy chain comprising an amino acid sequence selected from the group consisting of 2B12-H0, -H1, -H2, -H3 and -H4; and a light comprising an amino acid sequence selected from the group consisting of 2B12-L0, -L1, -L2, -L3 and -L4; (b) buffer system, e.g. sodium phosphate, sodium citrate, sodium borate; (c) isotonic agent, optionally NaCl; and (d) polysorbate 80, at a pH of between 6.5 and 8, optionally about 7.4. In one aspect, provided is a pharmaceutically acceptable and active formulation comprising (a) about 0.05 mg/mL to about 10 mg/mL of antibody; (b) about 10 mM buffer, e.g. sodium phosphate, sodium citrate, sodium borate; (c) isotonic agent, optionally about 9 mg/ml NaCl; and (d) polysorbate 80, at a pH of between 6.5 and 8, optionally about 7.4.

In one aspect provided is a humanized 10G5 monoclonal antibody comprising:
(a) a heavy chain CDR 1, 2 and 3 (HCDR1, HCDR2, HCDR3) comprising a sequence of SEQ ID NO: 2 (HCDR1), SEQ ID NO: 3 (HCDR2) and SEQ ID NO: 4 (HCDR3) respectively, and
(b) a light chain CDR 1, 2 and 3 (LCDR1, LCDR2, LCDR3) comprising a sequence of SEQ ID NO: 5, 6 and 7, respectively. Optionally, the antibody has a heavy chain human acceptor framework of VH1 subgroup combined with a JH6 subgroup, and a light chain human acceptor framework of VK1 subgroup combined with a JK2 subgroup. Optionally, the antibody has a heavy chain having a human acceptor framework comprising a substitution (e.g. a back-mutation).

Optionally, in any embodiments herein of a 10G5 antibody, the heavy chain framework may have one or more substitutions at position(s) selected from the group consisting of: residues 5, 11, 12, 13, 20, 38, 40, 48, 66, 67, 69, 71, 72a and 75 (Abnum numbering), including any combinations thereof. Optionally, in any embodiments herein of a 10G5 antibody, the light chain framework has one or more substitutions at position(s) selected from the group consisting of: residues 17, 18, 40, 45, 48, 70, 76 and 100 (Abnum numbering), including any combinations thereof. In one embodiment, a substitution(s) is a back mutation.

In one embodiment, provided is a humanized 10G5 monoclonal antibody comprising:
(a) a heavy chain variable region comprising an amino acid sequence selected from the group consisting of 10G5-H0, -H1, -H2, -H3, -H4, -H5 and -H6; and
(b) a light chain variable region comprising an amino acid sequence selected from the group consisting of 10G5-L0, -L1, -L2, -L3, -L4 and -L5.

In one embodiment, provided is a humanized 10G5 monoclonal antibody comprising:
(a) a heavy chain variable region comprising an amino acid sequence selected from the group consisting of SEQ ID NOS: 13-17, and
(b) a light chain variable region comprising an amino acid sequence selected from the group consisting of SEQ ID NOS: 8-12.

In one embodiment, provided is a humanized 10G5 monoclonal antibody comprising:
(a) a heavy chain variable region comprising an amino acid sequence of SEQ ID NO: 13, and
(b) a light chain variable region comprising an amino acid sequence of SEQ ID NO: 8.

In one embodiment, provided is a humanized 10G5 monoclonal antibody comprising:
(a) a heavy chain variable region comprising an amino acid sequence of SEQ ID NO: 14, and
(b) a light chain variable region comprising an amino acid sequence of SEQ ID NO: 9.

In one embodiment, provided is a humanized 10G5 monoclonal antibody comprising:
(a) a heavy chain variable region comprising an amino acid sequence of SEQ ID NO: 15, and
(b) a light chain variable region comprising an amino acid sequence of SEQ ID NO: 9.

In one aspect, provided is a pharmaceutically acceptable and active formulation comprising (a) about 0.05 mg/mL to about 10 mg/mL of an IgG antibody molecule comprising a heavy chain comprising an amino acid sequence selected from the group consisting of 10G5-H0, -H1, -H2, -H3, -H4, -H5 and H6 and a light chain comprising an amino acid sequence selected from the group consisting of 10G5-L0, -L1, -L2, -L3, -L4 and L5; (b) buffer system, e.g. sodium phosphate, sodium citrate, sodium borate; (c) isotonic agent, optionally NaCl; and (d) polysorbate 80, at a pH of between 6.5 and 8, optionally about 7.4. In one aspect, provided is a pharmaceutically acceptable and active formulation comprising (a) about 0.05 mg/mL to about 10 mg/mL of antibody; (b) about 10 mM buffer, e.g. sodium phosphate, sodium citrate, sodium borate; (c) isotonic agent, optionally about 9 mg/ml NaCl; and (d) polysorbate 80, at a pH of between 6.5 and 8, optionally about 7.4. In one embodiment, the antibodies bind to 1, 2, 3, 4 or 5 of the KIR3DL2 polypeptides alleles *002, *003, *005, *007, and/or *008. Optionally, the antibodies have an EC50 of no more than 5 µg/ml, optionally no more than 3 µg/ml, no more than 2 µg/ml, no more than 1 µg/ml or no more than 0.5 µg/ml for binding to cells made to express at their surface a particular KIR3DL2 allele (e.g alleles *001, *002, *003, *005, *007 and/or *008). In one aspect provided are antibodies that bind the KIR3DL2 polypeptide in the ligand (HLA) binding region (e.g. HLA binding pocket) or at least partly on the HLA binding face of KIR3DL2 protein.

In one aspect provided are antibodies that bind an epitope comprising residues I60 and/or G62 (with reference to SEQ ID NO: 1), and/or the antibodies have reduced binding to a KIR3DL2 polypeptide having a mutation at residues I60 and/or G62 (with reference to SEQ ID NO: 1, e.g. I60N, G62S). In one aspect provided are antibodies that bind an epitope comprising residues R13, A25 and/or Q27 of the KIR3DL2 polypeptide, and/or have reduced binding to a KIR3DL2 polypeptide having a mutation at residues R13, A25 and/or Q27 (with reference to SEQ ID NO: 1). For example, an antibody can have reduced binding to a KIR3DL2 polypeptide having the mutations R13W, A25T and/or Q27R. Optionally, the epitope additionally or alternatively comprises one or more of residues P14, S15 and/or H23 (with reference to SEQ ID NO: 1), and/or the antibodies have reduced binding to a KIR3DL2 polypeptide having a mutation at residues P14, S15 and/or H23 (with reference to SEQ ID NO: 1, e.g. P14S, S15A, H23S).

In other aspects, the invention provides for pharmaceutical compositions comprising such agents and a carrier, and for conjugates comprising such agents conjugated to e.g. a cytotoxic or detectable agent. In other aspects, the invention provides for nucleic acids and vectors encoding such agents, and host cells containing such nucleic acids and/or vectors. Also provided for are recombinant methods of producing the agents by culturing such host cells so that the nucleic acids are produced. In other aspects, the invention provides for articles of manufacture comprising a container comprising such agents and instructions directing a user to treat a disorder such as cancer or autoimmune disease in a patient. Optionally, the article may comprise another container containing another agent, wherein the instructions direct the user to treat the disorder with the antibody in combination with the agent. The invention also provides for methods of using the agents of the invention in the treatment of disorders such as cancer, an inflammatory disorder or an autoimmune disorder in a patient, optionally in conjunction with another anti-cancer or anti-inflammatory agent.

These and additional advantageous aspects and features of the invention may be further described elsewhere herein.

DETAILED DESCRIPTION OF THE INVENTION

Introduction

Figure 1A:
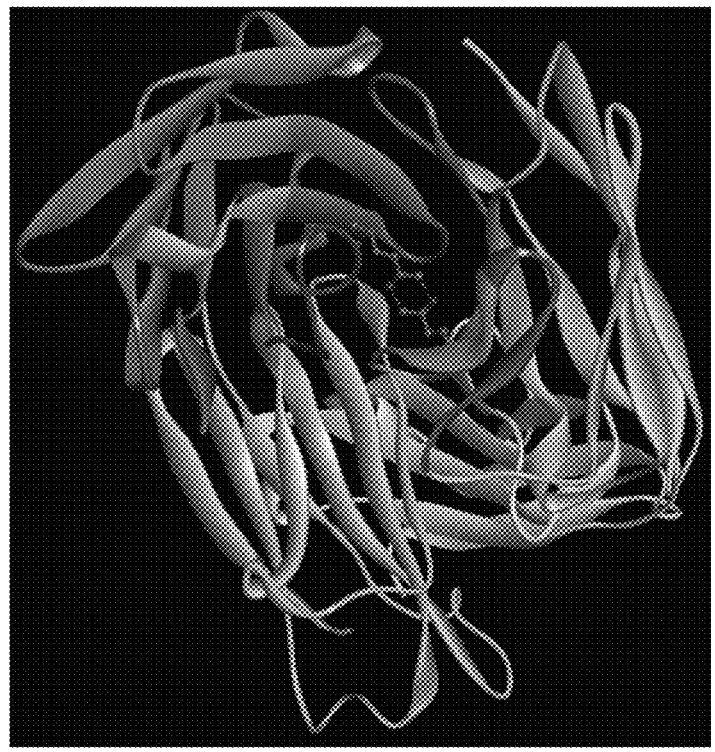
FIGS. 1A and 1B show modelling of the antibody structure, showing that when a glutamine is present in the light chain at residue 38 and heavy chain at residue 39, H-bonds may be built between VH_Q39 and VL_Q38, which may explain the greater physical stability of such antibodies.

The antibodies of the disclosure are able to directly and specifically target KIR3DL2-expressing cells, notably CD4+, KIR3DL2+ T cells, without targeting other cells such as KIR3DL1+ cells (or KIR3DL2+ KIR3DL1+ cells, KIR3DS1+ cells; or KIR3DS1 KIR3DL2+ cells), and do not internalize into KIR3DL2+ cells. Also provided are antibodies that inhibit binding of natural ligands of KIR3DL2 (or ligand-induced KIR3DL2 signaling). The disclosure provides antibodies having such properties, and which compete with each other for binding to a region of KIR3DL2+ that includes domains 0 defined by amino acid residues 1-98 of the mature KIR3DL2 polypeptides of SEQ ID NO: 1.

KIR3DL2 (CD158k) is a disulphide-linked homodimer of three-Ig domain molecules of about 140 kD, described in Pende et al. (1996) J. Exp. Med. 184: 505-518, the disclosure of which is incorporated herein by reference. KIR3DL1 (CD158e1) is a monomeric molecule of about 70 kD, described in Colonna and Samaridis (1995) Science 268 (5209), 405-408; the HLA binding pocket has been described in Vivian et al. (2011) Nature 479: 401-405. Natural ligands of KIR3DL2 include, inter alia, HLA-A and HLA-B polypeptides, notably HLA-A3 and HLA-A11 (see Hansasuta et al. (2004) Eur. J. Immunol. 34: 1673-1679 and HLA-B27. HLA-B27 (see, e.g., Weiss et al. (1985) Immunobiology 170(5):367-380 for organization, sequence and expression of the HLA-B27 gene, and for HLA-B27 multimers and HLA-B27$_2$ homodimers see Allen et al. (1999) J. Immunol. 162: 5045-5048 and Kollnberger et al (2007) Eur. J. Immunol. 37: 1313-1322. As used herein, "KIR3D" refers to any KIR3D receptor (e.g. KIR3DL1, KIR3DL2, KIR3DS1) individually or collectively, and the term "KIR3D" may be substituted by the term "KIR3DL1, KIR3DL2 and/or KIR3DS1". Similarly, "KIR3DL" refers to any KIR3DL receptor (e.g. KIR3DL1, KIR3DL2) individually or collectively, and the term "KIR3DL" may be substituted by the term "KIR3DL1 and/or KIR3DL2". The terms "KIR3D", "KIR3DL", "KIR3DL1", "KIR3DL2", "KIR3DS1" each furthermore include any variant, derivative, or isoform of the KIR3D gene or encoded protein(s) to which they refer. Several allelic variants have been reported for KIR3D polypeptides (e.g. KIR3DL2), each of these are encompassed by the respective terms. The amino acid sequence of the mature human KIR3DL2 (allele *002) is shown in SEQ ID NO: 1, corresponding to Genbank accession no. AAB52520 in which the 21 amino acid residue leader sequence has been omitted, and corresponding to IPD KIR database (published by the EMBL-EBI, European Bioinformatics Institute, United Kingdom) accession no. KIR00066.

```
                                              SEQ ID NO: 1
LMGGQDKPFL  SARPSTVVPR  GGHVALQCHY  RRGFNNFMLY

KEDRSHVPIF  HGRIFQESFI  MGPVTPAHAG  TYRCRGSRPH

SLTGWSAPSN  PLVIMVTGNH  RKPSLLAHPG  PLLKSGETVI

LQCWSDVMFE  HFFLHREGIS  EDPSRLVGQI  HDGVSKANFS

IGPLMPVLAG  TYRCYGSVPH  SPYQLSAPSD  PLDIVITGLY

EKPSLSAQPG  PTVQAGENVT  LSCSSWSSYD  IYHLSREGEA

HERRLRAVPK  VNRTFQADFP  LGPATHGGTY  RCFGSFRALP

CVWSNSSDPL  LVSVTGNPSS  SWPSPTEPSS  KSGICRHLHV

LIGTSVVIFL  FILLLFFLLY  RWCSNKKNAA  VMDQEPAGDR

TVNRQDSDEQ  DPQEVTYAQL  DHCVFIQRKI  SRPSQRPKTP

LTDTSVYTEL  PNAEPRSKVV  SCPRAPQSGL  EGVF
```

The cDNA of KIR3DL2 (allele *002) is shown in Genbank accession no. U30272. The precursor amino acid sequence (including leader sequence) of a human KIR3DL2 allele *002 is shown in Genbank accession no. AAB52520. The amino acid sequence of a human KIR3DL2 allele *001 is shown in IPD KIR database accession no. KIR00065. The amino acid sequence of a human KIR3DL2 allele *003 is shown in Genbank accession no. AAB36593 and IPD KIR database accession no. KIR00067. The amino acid sequence of a human KIR3DL2 allele *004 is shown in IPD KIR database accession no. KIR00068. The amino acid sequence of a human KIR3DL2 allele *005 is shown in IPD KIR database accession no. KIR00069. The amino acid sequence of a human KIR3DL2 allele *006 (mature) is shown in Genbank accession no. AAK30053 and IPD KIR database accession no. KIR00070. The amino acid sequence of a human KIR3DL2 allele *007 (mature) is shown in Genbank accession no. AAK30052 and IPD KIR database accession no. KIR00071. The amino acid sequence of a human KIR3DL2 allele *008 is shown in Genbank accession no. AAK30054 and IPD KIR database accession no. KIR00072. The amino acid sequence of a human KIR3DL2 allele *009 is shown in IPD KIR database accession no. KIR00457. The amino acid sequence of a human KIR3DL2 allele *011 is shown in IPD KIR database accession no. KIR00544. The cDNA encoding a KIR3DL1 (CD158e2) polypeptide (allele *00101) is shown in Genbank accession no. L41269; the encoded amino acid sequence is shown in Genbank accession no. AAA69870. Where a leader sequence is present in a particular SEQ ID NO describing a KIR3DL2 polypeptide sequence, any reference to amino acid residue positions herein will be to the mature KIR3DL polypeptide. Each of the database records having the above accession numbers are incorporated herein by reference.

Provided are methods of using the antigen-binding compounds; for example, a method for inhibiting cell proliferation or activity, for delivering a molecule into a cell (e.g. a toxic molecule, a detectable marker, etc.), for targeting, identifying or purifying a cell, for depleting, killing or eliminating a cell, for reducing cell proliferation, the method comprising exposing a cell, such as a T cell which expresses a KIR3DL2 polypeptide, to an antigen-binding compound of the disclosure that binds a KIR3DL2 polypeptide. It will be appreciated that for the purposes of the present disclosure, "cell proliferation" can refer to any aspect of the growth or proliferation of cells, e.g., cell growth, cell division, or any aspect of the cell cycle. The cell may be in cell culture (in vitro) or in a mammal (in vivo), e.g. a mammal suffering from a KIR3DL2-expressing pathology. Also provided is a method for inducing the death of a cell or inhibiting the proliferation or activity of a cell which expresses a KIR3DL2 polypeptide, comprising exposing the cell to an antigen-binding compound that binds a KIR3DL2 polypeptide linked to a toxic agent, in an amount effective to induce death and/or inhibit the proliferation or activity of the cell. Thus, provided is a method for treating a mammal suffering from a proliferative disease, and any condition characterized by a pathogenic expansion or activation of cells expressing of a KIR3DL2 polypeptide, the method comprising administering a pharmaceutically effective amount of an antigen-binding compound disclosed herein to the mammal. Examples of such conditions include Sezary Syndrome, Mycosis Fungoides, CTCL, a peripheral T cell lymphoma, an ortho visceral extranodal PTCL (e.g., an NK/T-lymphoma or an enteropathy associated T cell lymphoma (EATL)), an anaplastic large cell lymphoma (ALCL), a PTCL-NOS (Not Otherwise Specified), and autoimmune or inflammatory conditions, e.g. arthritis, ankylosing spondylitis, cardiovascular disease.

Provided are methods for producing and using antibodies and other compounds suitable for the treatment of disorders (e.g. cancers, inflammatory and autoimmune disorders) where eliminating KIR3DL2-expressing cells would be useful. Antibodies, antibody derivatives, antibody fragments, and cell producing them are encompassed, as are methods of producing the same and methods of treating patients using the antibodies and compounds.

Since the present antibodies are specific for KIR3DL2, they can be used for a range of purposes, including purifying KIR3DL2 or KIR3DL2-expressing cells, modulating (e.g. activating or inhibiting) KIR3DL2 receptors in vitro, ex vivo, or in vivo, targeting KIR3DL2-expressing cells for destruction in vivo, or specifically labeling/binding KIR3DL2 in vivo, ex vivo, or in vitro, including for methods such as immunoblotting, IHC analysis, i.e. on frozen biopsies, FACS analysis, and immunoprecipitation.

Definitions

As used in the specification, "a" or "an" may mean one or more. As used in the claim(s), when used in conjunction with the word "comprising", the words "a" or "an" may mean one or more than one. As used herein "another" may mean at least a second or more.

Where "comprising" is used, this can optionally be replaced by "consisting essentially of" or by "consisting of".

The terms "cancer" and "tumor" as used herein are defined as a new growth of cells or tissue comprising uncontrolled and progressive multiplication. In a specific embodiment, upon a natural course the cancer is fatal. In specific embodiments, a cancer is invasive, metastatic, and/or anaplastic (loss of differentiation and of orientation to one another and to their axial framework).

"Autoimmune" disorders include any disorder, condition, or disease in which the immune system mounts a reaction against self cells or tissues, due to a breakdown in the ability to distinguish self from non-self or otherwise. Examples of autoimmune disorders include rheumatoid arthritis, rheumatoid vascularitis, systemic lupus erythematosus, multiple sclerosis, Wegener's granulomatosus, spondylarthritis, and others. An "inflammatory disorder" includes any disorder characterized by an unwanted immune response. Autoimmune and inflammatory disorders can involve any component of the immune system, and can target any cell or tissue type in the body.

The term "antibody," as used herein, refers to polyclonal and monoclonal antibodies. Depending on the type of constant domain in the heavy chains, antibodies are assigned to one of five major classes: IgA, IgD, IgE, IgG, and IgM. Several of these are further divided into subclasses or isotypes, such as IgG1, IgG2, IgG3, IgG4, and the like. An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids that is primarily responsible for antigen recognition. The terms variable light chain ($V_L$) and variable heavy chain ($V_H$) refer to these light and heavy chains respectively. The heavy-chain constant domains that correspond to the different classes of immunoglobulins are termed "alpha," "delta," "epsilon," "gamma" and "mu," respectively. The subunit structures and three-dimensional configurations of different classes of immunoglobulins are well known. IgG and/or IgM are the preferred classes of antibodies employed herein, with IgG being particularly preferred, because they are the most common antibodies in the physiological situation and because they are most easily made in a laboratory setting. Preferably the antibody is a monoclonal antibody. Particularly preferred are humanized, chimeric, human, or otherwise-human-suitable antibodies. "Antibodies" also includes any fragment or derivative of any of the herein described antibodies.

The term "specifically binds to" means that an antibody can bind preferably in a competitive binding assay to the binding partner, e.g. KIR3DL2, as assessed using either recombinant forms of the proteins, epitopes therein, or native proteins present on the surface of isolated target cells. Competitive binding assays and other methods for determining specific binding are further described below and are well known in the art.

When an antibody is said to "compete with" a particular monoclonal antibody (e.g. 2B12, 10G5), it means that the antibody competes with the monoclonal antibody in a binding assay using either recombinant KIR3DL2 molecules or surface expressed KIR3DL2 molecules. For example, if a test antibody reduces the binding of 2B12 or 10G5 to a KIR3DL2 polypeptide or KIR3DL2-expressing cell in a binding assay, the antibody is said to "compete" respectively with 2B12 or 10G5.

The term "affinity", as used herein, means the strength of the binding of an antibody to an epitope. The affinity of an antibody is given by the dissociation constant Kd, defined as $[Ab] \times [Ag]/[Ab\text{-}Ag]$, where [Ab-Ag] is the molar concentration of the antibody-antigen complex, [Ab] is the molar concentration of the unbound antibody and [Ag] is the molar concentration of the unbound antigen. The affinity constant $K_a$ is defined by 1/Kd. Examples of methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One standard method well known in the art for determining the affinity of mAbs is the use of surface plasmon resonance (SPR) screening (such as by analysis with a BIAcore™ SPR analytical device).

As used herein, a "determinant" designates a site of interaction or binding on a polypeptide.

The term "epitope" refers to an antigenic determinant, and is the area or region on an antigen to which an antibody binds. A protein epitope may comprise amino acid residues directly involved in the binding as well as amino acid residues which are effectively blocked by the specific antigen binding antibody or peptide, i.e., amino acid residues within the "footprint" of the antibody. It is the simplest form or smallest structural area on a complex antigen molecule that can combine with e.g., an antibody or a receptor. Epitopes can be linear or conformational/structural. The term "linear epitope" is defined as an epitope composed of amino acid residues that are contiguous on the linear sequence of amino acids (primary structure). The term "conformational or structural epitope" is defined as an epitope composed of amino acid residues that are not all contiguous and thus represent separated parts of the linear sequence of amino acids that are brought into proximity to one another by folding of the molecule (secondary, tertiary and/or quaternary structures). A conformational epitope is dependent on the 3-dimensional structure. The term 'conformational' is therefore often used interchangeably with 'structural'.

The term "intracellular internalization", or "internalization" when referring to a KIR3DL2 polypeptide and/or antibody that binds such, refers to the molecular, biochemical and cellular events associated with the process of translocating a molecule from the extracellular surface of a cell to the intracellular surface of a cell. The processes responsible for intracellular internalization of molecules are well-known and can involve, inter alia, the internalization of extracellular molecules (such as hormones, antibodies, and small organic molecules); membrane-associated molecules (such as cell-surface receptors); and complexes of membrane-associated molecules bound to extracellular molecules (for example, a ligand bound to a transmembrane receptor or an antibody bound to a membrane-associated molecule). Thus, "inducing and/or increasing intracellular internalization" comprises events wherein intracellular internalization is initiated and/or the rate and/or extent of intracellular internalization is increased.

The term "depleting", with respect to KIR3DL2-expressing cells means a process, method, or compound that can kill, eliminate, lyse or induce such killing, elimination or lysis, so as to negatively affect the number of KIR3DL2-expressing cells present in a sample or in a subject.

The term "agent" is used herein to denote a chemical compound, a mixture of chemical compounds, a biological macromolecule, or an extract made from biological materials. The term "therapeutic agent" refers to an agent that has biological activity.

The terms "toxic agent" and "cytotoxic agent" encompass any compound that can slow down, halt, or reverse the proliferation of cells, decrease their activity in any detectable way, or directly or indirectly kill them. Preferably, cytotoxic agents cause cell death primarily by interfering directly with the cell's functioning, and include, but are not limited to, alkylating agents, tumor necrosis factor inhibitors, intercalators, microtubule inhibitors, kinase inhibitors, proteasome inhibitors and topoisomerase inhibitors. A "toxic payload" as used herein refers to a sufficient amount of cytotoxic agent which, when delivered to a cell results in cell death. Delivery of a toxic payload may be accomplished by administration of a sufficient amount of immunoconjugate comprising an antibody or antigen binding fragment and a cytotoxic agent. Delivery of a toxic payload may also be accomplished by administration of a sufficient amount of an immunoconjugate comprising a cytotoxic agent, wherein the immunoconjugate comprises a secondary antibody or antigen binding fragment thereof which recognizes and binds an antibody or antigen binding fragment.

For the purposes herein, a "humanized" or "human" antibody refers to an antibody in which the constant and variable framework region derived from one or more human immunoglobulins is fused with the binding region, e.g. the CDR, of an animal immunoglobulin. Such antibodies are designed to maintain the binding specificity of the non-human antibody from which the binding regions are derived, but to avoid an immune reaction against the non-human antibody. Such antibodies can be obtained from transgenic mice or other animals that have been "engineered" to produce specific human antibodies in response to antigenic challenge (see, e.g., Green et al. (1994) Nature Genet 7:13; Lonberg et al. (1994) Nature 368:856; Taylor et al. (1994) Int Immun 6:579, the entire teachings of which are herein incorporated by reference). A fully human antibody also can be constructed by genetic or chromosomal transfection methods, as well as phage display technology, all of which are known in the art (see, e.g., McCafferty et al. (1990) Nature 348:552-553). Human antibodies may also be generated by in vitro activated B cells (see, e.g., U.S. Pat. Nos. 5,567,610 and 5,229,275, which are incorporated in their entirety by reference).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The terms "Fc domain," "Fc portion," and "Fc region" refer to a C-terminal fragment of an antibody heavy chain, e.g., from about amino acid (aa) 230 to about aa 450 of human γ (gamma) heavy chain or its counterpart sequence in other types of antibody heavy chains (e.g., a, 6, c and g for human antibodies), or a naturally occurring allotype thereof.

The term "antibody-dependent cell-mediated cytotoxicity" or "ADCC" is a term well understood in the art, and refers to a cell-mediated reaction in which non-specific cytotoxic cells that express Fc receptors (FcRs) recognize a bound antibody on a target cell and subsequently cause lysis of the target cell. Non-specific cytotoxic cells that mediate ADCC include natural killer (NK) cells, macrophages, monocytes, neutrophils, and eosinophils.

The terms "isolated", "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under expressed or not expressed at all.

The term "modification" when referring to a sequence of amino acids (e.g., "amino acid modification"), is meant an amino acid substitution, insertion, and/or deletion in a polypeptide sequence. By "modification" or "amino acid modification" is meant an amino acid substitution, insertion, and/or deletion in a polypeptide sequence. By "amino acid substitution" or "substitution" herein is meant the replacement of an amino acid at a given position in a protein sequence with another amino acid. For example, the substitution P14S refers to a variant of a parent polypeptide, in which the proline at position 14 is replaced with serine. A "variant" of a polypeptide refers to a polypeptide having an amino acid sequence that is substantially identical to a reference polypeptide, typically a native or "parent" polypeptide. The polypeptide variant may possess one or more amino acid substitutions, deletions, and/or insertions at certain positions within the native amino acid sequence.

As used herein, the term antibody that "binds" a polypeptide or epitope designates an antibody that binds said determinant with specificity and/or affinity.

The term "identity" or "identical", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

Antibodies and Epitopes

The present invention is based, in part, on the discovery of modified human acceptor framework sequences into which antibody CDRs can be incorporated such that the resulting anti-KIR3DL2 variable region retains the ability to bind the D0 domain of human KIR3DL2.

Such humanized variable regions and antibodies containing them can bind a segment of KIR3DL2 (SEQ ID NO: 1) comprising residues I60 and/or G62. Optionally, the antibodies bind an epitope comprising one or more of residues I60 and/or G62, but not residues R13, A25, and/or Q27. Optionally, the antibodies bind an epitope comprising one or more of residues I60 and/or G62 as well as one or more of residues P14, S15 and/or H23.

Unless otherwise specified, the Abnum amino acid numbering nomenclature for immunoglobulins is used throughout this disclosure (see Abhinandan and Martin, (2008) Molecular Immunology 45: 3832-3839, the disclosure of which is incorporated by reference). Sequence numbering using the Abnum system can also be automatically generated at http://www.bioinfo.org.uk/abs/abnum. However it will be appreciated that the person of skill in the art can use an alternative numbering system and identify positions corresponding to Abnum numbering. For residues 38 and 39 in the respective heavy and light chains, the Abnum position corresponds to the same positions in the Kabat numbering system (Kabat et al. (1991) Sequences of Protein of Immunological Interest, 5th ed., United States Public Health Service, National Institute of Health, Bethesda, Md.).

When the antibody comprises a glutamine at residue 38 in the VL domain sequence, preferred human VH acceptor frameworks comprise a glutamine at residue 39 in the VH domain sequence.

In one embodiment, the humanized antibody comprises a heavy chain framework from the human subgroup VH1 together with JH6, optionally the antibodies comprises IGHV1-46*03, together with IGHJ6*01. In one embodiment, the humanized antibody comprises a light chain framework from the human subgroup VK1, optionally IGKV1-NL1*01.

In one embodiment, the humanized antibody comprises a heavy chain framework from the human subgroup VH1 and/VH7, together with JH6, optionally the antibodies comprises IGHV7-4-1*02 and IGHV1-c*01, together with IGHJ6*01. In one embodiment, the humanized antibody comprises a light chain framework from the human subgroup VK1 and VK4, optionally IGKV4-1*01 and IGKV1-39*01, together with JH4, optionally IGKJ4*01.

The humanized antibody may further comprise one or more back-mutations in the human framework sequences, to, e.g., enhance affinity, stability, or other properties of the humanized antibody.

In another aspect, provided are particular humanized antibodies that are humanized versions of 2B12 or 10G5. Such antibodies are typically characterized by comprising key amino acid residues from 2B12 or 10G5 CDRs in human framework sequences.

Antibody 10G5

Examples of humanized VH and VL amino acid sequences of antibody 10G5 are shown in SEQ ID NOS: 13-17 and 8-12, respectively. In one aspect, provided is an isolated humanized antibody that binds a human KIR3DL2 polypeptide, wherein the antibody comprises: a HCDR1 region comprising an amino acid sequence SYTMH as set forth in SEQ ID NO: 2, or a sequence of at least 3 or 4 amino acids thereof; a HCDR2 region comprising an amino acid sequence YINPSSGYTENNRKF as set forth in SEQ ID NO: 3, or a sequence of at least 4, 5, 6, 7, 8, 9 or 10 contiguous amino acids thereof; a HCDR3 region comprising an amino acid sequence LGKGLLPPFDY as set forth in SEQ ID NO: 4, or a sequence of at least 4, 5, 6, 7, 8, 9 or 10 contiguous amino acids thereof; a LCDR1 region comprising an amino acid sequence RASENIYSNLA as set forth in SEQ ID NO: 5, or a sequence of at least 4, 5, 6, 7, 8, 9 or 10 contiguous amino acids thereof; a LCDR2 region comprising an amino acid sequence AATNLAD as set forth in SEQ ID NO: 6, or a sequence of at least 3, 4 or 5 contiguous amino acids thereof; a LCDR3 region comprising an amino acid sequence QHFWGTPYT as set forth in SEQ ID NO: 7, or a sequence of at least 5, 6, 7, or 8 contiguous amino acids thereof.

In one aspect, the invention provides an isolated humanized 10G5 antibody that binds a human KIR3DL2 polypeptide, comprising:
(a) a CDR-H1 comprising the amino acid sequence of SEQ ID NO:2;
(b) a CDR-H2 comprising the amino acid sequence of SEQ ID NO:3;

(c) a CDR-H3 comprising the amino acid sequence of SEQ ID NO:4;
(d) a CDR-L1 comprising the amino acid sequence of SEQ ID NO:5;
(e) a CDR-L2 comprising the amino acid sequence of SEQ ID NO:6;
(f) a CDR-L3 comprising the amino acid sequence of SEQ ID NO:7; and
(g) human framework sequences.

In one embodiment, the humanized antibody comprises a heavy chain framework from the human subgroup VH1 together with JH6, optionally the antibodies comprises IGHV1-46*03, together with IGHJ6*01. In one embodiment, the humanized antibody comprises a light chain framework from the human subgroup VK1, optionally IGKV1-NL1*01.

Optionally the human framework comprises one or more mutations, e.g. back mutations. Example 1 shows identification of frameworks and back mutations for 10G5 variable regions. As compared to chimeric 10G5, these mutants tested showed a comparable binding profile at the two mAb concentrations used in the assay. Embodiments of the invention thus include the back-mutated 10G5 heavy chain variants having back mutations at any one or more (or any combination of) the following residues, using Abnum numbering:

10G5 VH: 5, 11, 12, 13, 20, 38, 40, 48, 66, 67, 69, 71, 72a, 75.

Further embodiments of the invention thus include the back-mutated 10G5 light chain variants having back mutations at any one or more (or any combination of) the following residues:

10G5 VL: 17, 18, 40, 45, 48, 70, 76, 100.

The humanized antibody may further comprise one or more additional mutations (e.g. back-mutations) in the human framework sequences, to, e.g., enhance affinity, stability, or other properties of the humanized antibody.

In one aspect, provided is an isolated humanized 10G5 antibody that binds human KIR3DL2 polypeptide, comprising:
(a) a CDR-H1 comprising the amino acid sequence of SEQ ID NO: 2;
(b) a CDR-H2 comprising the amino acid sequence of SEQ ID NO: 3;
(c) a CDR-H3 comprising the amino acid sequence of SEQ ID NO: 4;
(d) a CDR-L1 comprising the amino acid sequence of SEQ ID NO: 5;
(e) a CDR-L2 comprising the amino acid sequence of SEQ ID NO: 6;
(f) a CDR-L3 comprising the amino acid sequence of SEQ ID NO: 7; and
(g) human framework sequences, wherein a glutamine (Q) residue is present at position 39 of the VH domain and at position 38 of the VL domain. Optionally, the human framework sequences further comprise one or more back-mutations.

The glutamine (Q) residue at position 39 may exist naturally in the human VH framework sequence, or may be introduced by amino acid substitution or other modification of the sequence.

In another aspect, the invention provides humanized antibodies that comprise a VH domain having at least about 80% sequence identity (e.g., at least about 85%, 90%, 95%, 97%, 98%, or more identity) to the VH domain of 10G5 of SEQ ID NOS: 13-17. In another particular aspect, the invention provides a humanized antibody that binds KIR3DL2, comprising (a) a VH domain that comprises non-human CDR residues incorporated into a human VH domain, wherein the VH domain is at least about 80% (such as at least 90%, 95%, 97%, 98%) identical to a humanized 10G5 VH of SEQ ID NOS: 13-17, and (b) (a) a VL domain that comprises non-human CDR residues incorporated into a human VL domain, wherein the VL domain is at least about 80% (such as at least 90%, 95%, 97%, 98%) identical to humanized 10G5 VL of SEQ ID NOS: 8-12.

Antibody 2B12

Examples of humanized VH and VL amino acid sequences of antibody 2B12 are shown in SEQ ID NOS: 24-28 and 29-33, respectively. In one aspect, provided is an isolated humanized antibody that binds a human KIR3DL2 polypeptide, wherein the antibody comprises: a HCDR1 region comprising an amino acid sequence TAGMQ as set forth in SEQ ID NO: 18, or a sequence of at least 3 or 4 contiguous amino acids thereof; a HCDR2 region comprising an amino acid sequence WINSHSGVPKYAEDFK as set forth in SEQ ID NO: 19, or a sequence of at least 4, 5, 6, 7, 8, 9 or 10 contiguous amino acids thereof; a HCDR3 region comprising an amino acid sequence GGDEGVMDY as set forth in SEQ ID NO: 20, or a sequence of at least 5, 6, 7, or 8 contiguous amino acids thereof; a LCDR1 region comprising an amino acid sequence KASQDVSTAVA as set forth in SEQ ID NO: 21, or a sequence of at least 4, 5, 6, 7, 8, 9 or 10 contiguous amino acids thereof; a LCDR2 region comprising an amino acid sequence WTSTRHT as set forth in SEQ ID NO: 22, or a sequence of at least 3, 4 or 5 contiguous amino acids thereof; and/or a LCDR3 region comprising an amino acid sequence QQHYSTPWT as set forth in SEQ ID NO: 23, or a sequence of at least 4, 5, 6, 7, or 8 contiguous amino acids thereof.

In any of the embodiments herein, any of the CDRs 1, 2 and 3 of the heavy and light chains may be characterized by a sequence of at least 4, 5, 6, 7, 8, 9 or 10 contiguous amino acids thereof, and/or as having an amino acid sequence that shares at least 70%, 80%, 85%, 90% or 95% sequence identity with the particular CDR or set of CDRs listed in the corresponding SEQ ID NO.

In one aspect, the invention provides an isolated humanized 2B12 antibody that binds a human KIR3DL2 polypeptide, comprising:
(a) a CDR-H1 comprising the amino acid sequence of SEQ ID NO: 18;
(b) a CDR-H2 comprising the amino acid sequence of SEQ ID NO: 19;
(c) a CDR-H3 comprising the amino acid sequence of SEQ ID NO: 20;
(d) a CDR-L1 comprising the amino acid sequence of SEQ ID NO: 21;
(e) a CDR-L2 comprising the amino acid sequence of SEQ ID NO: 22;
(f) a CDR-L3 comprising the amino acid sequence of SEQ ID NO: 23; and
(g) human framework sequences.

In one embodiment, the humanized antibody comprises a heavy chain framework from the human subgroup VH1 and/or VH7 together with JH6, optionally the antibodies comprises IGHV7-4-1*02 and/or IGHV1-c*01, together with IGHJ6*01. In one embodiment, the humanized antibody comprises a light chain framework from the human subgroup VK1 and/or VK4, optionally IGKV4-1*01 and/or IGKV1-39*01, together with JH4, optionally IGKJ4*01.

Optionally a human framework comprises one or more mutations, e.g. back mutations. Example 1 shows identification of frameworks and back mutations in the 2B12 variable regions. As compared to chimeric 2B12 these mutants tested showed a comparable binding profile at the two mAb concentrations used in the assay. Embodiments of the invention thus include the back-mutated 2B12 heavy chain variants having back mutations at any one or more (or any combination of) the following residues, using Abnum numbering:

2B12 VH: 2, 38, 39, 40, 43, 48, 68, 72c, 91, 108.

Further embodiments of the invention thus include the back-mutated 2B12 light chain variants having back mutations at any one or more (or any combination of) the following residues:

2B12 VL: 3, 8, 9, 21, 43, 71, 78, 104.

The humanized antibody may further comprise one or more additional mutations (e.g. back-mutations) in the human framework sequences, to, e.g., enhance affinity, stability, or other properties of the humanized antibody.

In one aspect, provided is an isolated humanized 2B12 antibody that binds human KIR3DL2 polypeptide, comprising:
(a) a CDR-H1 comprising the amino acid sequence of SEQ ID NO: 18;
(b) a CDR-H2 comprising the amino acid sequence of SEQ ID NO: 19;
(c) a CDR-H3 comprising the amino acid sequence of SEQ ID NO: 20;
(d) a CDR-L1 comprising the amino acid sequence of SEQ ID NO: 21;
(e) a CDR-L2 comprising the amino acid sequence of SEQ ID NO: 22;
(f) a CDR-L3 comprising the amino acid sequence of SEQ ID NO: 23; and
(g) human framework sequences, wherein a glutamine (Q) residue is present at position 39 of the VH domain and at position 38 of the VL domain. Optionally, the human framework sequences further comprise one or more back-mutations.

In another aspect, the invention provides humanized antibodies that comprise a VH domain having at least about 80% sequence identity (e.g., at least about 85%, 90%, 95%, 97%, 98%, or more identity) to the VH domain of 2B12 or humanized 2B12 of SEQ ID NOS: 29-33. In another particular aspect, the invention provides a humanized antibody that binds KIR3DL2, comprising (a) a VH domain that comprises non-human CDR residues incorporated into a human VH domain, wherein the VH domain is at least about 80% (such as at least 90%, 95%, 97%, 98%) identical to humanized 2B12 VH of SEQ ID NOS: 29-33, and (b) (a) a VL domain that comprises non-human CDR residues incorporated into a human VL domain, wherein the VL domain is at least about 80% (such as at least 90%, 95%, 97%, 98%) identical to humanized 2B12 VL of SEQ ID NOS: 24-28.

The glutamine (Q) residue at position 39 may exist naturally in the human VH framework sequence, or may be introduced by amino acid substitution or other modification of the sequence.

The 10G5 or 2B12 antibody may further comprise a human IgG constant domain (e.g. IgG1, IgG4). Optionally the constant domain is an IgG1 domain comprising a modification to increase Fc receptor binding. Optionally the constant domain is an IgG domain (e.g. IgG1, IgG4) comprising a modification to decrease Fc receptor binding.

For recombinant production of humanized antibodies, humanized VH and VL regions, or variant versions thereof, can be cloned into expression vectors encoding full-length or truncated constant regions from a human antibody according to standard recombinant methods (see, e.g., Sambrook et al., Molecular Cloning: A Laboratory Manual, 2$^{nd}$ Ed., Cold Spring Harbor Laboratory, Cold Spring Harbor, N.Y., 1989). The result is a transfected cell line that expresses and secretes the humanized antibody molecule of interest, comprising the selected VH and VL regions and constant regions. cDNA sequences encoding the constant regions of human antibodies are known.

If desired, the class of a humanized antibody may also be "switched" by known methods. Class switching techniques may be used to convert one IgG subclass to another, e.g., from IgG1 to IgG2. Thus, the effector function of the antibodies of the invention may be changed by isotype switching to, e.g., an IgG1, IgG2, IgG3, IgG4 antibody for various therapeutic uses.

Various forms of the humanized antibodies (e.g. 10G5 and 2B12) are contemplated. For example, the humanized antibody may be an antibody fragment, such as a Fab or other type of fragment described herein. Alternatively, the humanized antibody may be a full-length or intact antibody, such as a full-length or intact IgG1 or IgG4 antibody. The constant region may further be modified according to known methods. For example, in an IgG4 constant region, residue S241 may be mutated to a proline (P) residue to allow complete disulphide bridge formation at the hinge (see, e.g., Angal et al., Mol Immunol. 1993; 30:105-8).

In one embodiment, where KIR3DL2 blockade (e.g. inhibition of binding of KIR3DL2 by its HLA ligands) is desired without depletion (e.g. via CDC or ADCC) of the KIR3DL2 expressing cell, the humanized antibody is a full-length IgG4 antibody or a fragment thereof. In one embodiment, where depletion (e.g. via CDC or ADCC) of the KIR3DL2 expressing cell is desired, the humanized antibody is a full-length IgG1 antibody or a fragment thereof that comprises an Fc region that binds to Fc receptors (e.g. CD16). The antibody may further comprise a human IgG1 constant domain comprising a modification, e.g. to increase Fc receptor binding.

In view of the ability of the anti-KIR3DL2 antibodies (particularly the non-internalizing antibodies) to induce ADCC and CDC, the antibodies can also be made with modifications that increase their ability to bind Fc receptors which can affect effector functions such as antibody-dependent cytotoxicity, mast cell degranulation, and phagocytosis, as well as immunomodulatory signals such as regulation of lymphocyte proliferation and antibody secretion. Typical modifications include modified human IgG1 constant regions comprising at least one amino acid modification (e.g. substitution, deletions, insertions), and/or altered types of glycosylation, e.g., hypofucosylation. Such modifications can affect interaction with Fc receptors: FcγRI (CD64), FcγRII (CD32), and FcγRIII (CD 16). FcγRI (CD64), FcγRIIA (CD32A) and FcγRIII (CD 16) are activating (i.e., immune system enhancing) receptors while FcγRIIB (CD32B) is an inhibiting (i.e., immune system dampening) receptor. A modification may, for example, increase binding of the Fc domain to FcγRIIIa on effector (e.g. NK) cells. Examples of modifications are provided in PCT/EP2013/069302 filed 17 Sep. 2013, the disclosure of which is incorporated herein by reference.

In some embodiments, the antibodies comprising a variant Fc region comprise at least one amino acid modification (for example, possessing 1, 2, 3, 4, 5, 6, 7, 8, 9, or more amino acid modifications) in the CH3 domain of the Fc region. In other embodiments, the antibodies comprising a variant Fc region comprise at least one amino acid modification (for example, possessing 1, 2, 3, 4, 5, 6, 7, 8, 9, or more amino acid modifications) in the CH2 domain of the Fc region, which is defined as extending from amino acids 231-341. In some embodiments, antibodies comprise at least two amino acid modifications (for example, possessing 2, 3, 4, 5, 6, 7, 8, 9, or more amino acid modifications), wherein at least one such modification is in the CH3 region and at least one such modification is in the CH2 region. Encompasses also are amino acid modification in the hinge region. In one embodiment, encompassed are amino acid modification in the CH1 domain of the Fc region, which is defined as extending from amino acids 216-230. Any combination of Fc modifications can be made, for example any combination of different modifications disclosed in U.S. Pat. Nos. 7,632, 497; 7,521,542; 7,425,619; 7,416,727; 7,371,826; 7,355, 008; 7,335,742; 7,332,581; 7,183,387; 7,122,637; 6,821,505 and 6,737,056; in PCT Publications Nos. WO2011/109400; WO 2008/105886; WO 2008/002933; WO 2007/021841; WO 2007/106707; WO 06/088494; WO 05/115452; WO 05/110474; WO 04/1032269; WO 00/42072; WO 06/088494; WO 07/024249; WO 05/047327; WO 04/099249 and WO 04/063351; and in Lazar et al. (2006) Proc. Nat. Acad. Sci. USA 103(11): 405-410; Presta, L. G. et al. (2002) Biochem. Soc. Trans. 30(4):487-490; Shields, R. L. et al. (2002) J. Biol. Chem. 26; 277(30):26733-26740 and Shields, R. L. et al. (2001) J. Biol. Chem. 276(9):6591-6604).

Anti-KIR3DL2 antibodies may comprise a variant Fc region, wherein the variant Fc region comprises at least one amino acid modification (for example, possessing 1, 2, 3, 4, 5, 6, 7, 8, 9, or more amino acid modifications) relative to a wild-type Fc region, such that the molecule has an enhanced effector function relative to a molecule comprising a wild-type Fc region, optionally wherein the variant Fc region comprises a substitution at any one or more of positions 221, 239, 243, 247, 255, 256, 258, 267, 268, 269, 270, 272, 276, 278, 280, 283, 285, 286, 289, 290, 292, 293, 294, 295, 296, 298, 300, 301, 303, 305, 307, 308, 309, 310, 311, 312, 316, 320, 322, 326, 329, 330, 332, 331, 332, 333, 334, 335, 337, 338, 339, 340, 359, 360, 370, 373, 376, 378, 392, 396, 399, 402, 404, 416, 419, 421, 430, 434, 435, 437, 438 and/or 439. In one embodiment, anti-KIR3DL2 antibodies may comprise a variant Fc region, wherein the variant Fc region comprises at least one amino acid modification (for example, possessing 1, 2, 3, 4, 5, 6, 7, 8, 9, or more amino acid modifications) relative to a wild-type Fc region, such that the molecule has an enhanced effector function relative to a molecule comprising a wild-type Fc region, optionally wherein the variant Fc region comprises a substitution at any one or more of positions 239, 298, 330, 332, 333 and/or 334 (e.g. S239D, S298A, A330L, I332E, E333A and/or K334A substitutions).

In one embodiment, antibodies having variant or wild-type Fc regions may have altered glycosylation patterns that increase Fc receptor binding ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies to thereby produce an antibody with altered glycosylation. See, for example, Shields, R. L. et al. (2002) J. Biol. Chem. 277:26733-26740; Umana et al. (1999) Nat. Biotech. 17:176-1, as well as, European Patent No: EP 1,176,195; PCT Publications WO 06/133148; WO 03/035835; WO 99/54342, each of which is incorporated herein by reference in its entirety. In one aspect, the antibodies are hypofucosylated in their constant region. Such antibodies may comprise an amino acid alteration or may not comprise an amino acid alteration but be produced or treated under conditions so as to yield such hypofucosylation. In one aspect, an antibody composition comprises a chimeric, human or humanized antibody described herein, wherein at least 20, 30, 40, 50, 60, 75, 85, 90, 95% or substantially all of the antibody species in the composition have a constant region comprising a core carbohydrate structure (e.g. complex, hybrid and high mannose structures) which lacks fucose. In one embodiment, provided is an antibody composition which is free of antibodies comprising a core carbohydrate structure having fucose. The core carbohydrate will preferably be a sugar chain at Asn297.

Producing Anti-KIR3DL2 Antibodies

The antibodies may be produced by a variety of techniques known in the art. Typically, they are produced by immunization of a non-human animal, preferably a mouse, with an immunogen comprising a KIR3DL2 polypeptide, preferably a human KIR3DL2 polypeptide. Antibodies may also be produced by selection of combinatorial libraries of immunoglobulins.

The invention also provides isolated nucleic acids encoding the anti-KIR3DL2 antibodies described herein, as well as vectors and host cells comprising such nucleic acids. In one aspect, a nucleic acid fragment encoding the agent according to the invention is provided. In one aspect, a nucleic acid fragment encoding the agent according to the invention, which is selected from a DNA and an RNA fragment. Also provided for are methods of producing such anti-KIR3DL2 antibodies using recombinant techniques such as, e.g., culturing suitable host cells comprising such nucleic acids or vectors so that the nucleic acid is expressed and the humanized antibody produced. Before culturing, the host cell may, for example, be co-transfected with a vector comprising nucleic acids encoding a variable heavy domain and with a vector comprising nucleic acid encoding a variable light domain. Additionally, the antibody may be recovered and/or purified from the host cell culture using known techniques. Useful vectors, host cells, and techniques are further described below. Generally, for recombinant production of the antibody, a nucleic acid encoding it is isolated and inserted into a replicable vector for further cloning (amplification of the DNA) or for expression, typically operably linked to one or more expression control elements. DNA encoding the monoclonal antibody is readily isolated and sequenced using conventional procedures (e.g., by using oligonucleotide probes that are capable of binding specifically to genes encoding the heavy and light chains of the antibody). Many vectors are known and available. The vector components generally include, but are not limited to, one or more of the following: a signal sequence, an origin of replication, one or more marker genes, an enhancer element, a promoter, and a transcription-termination sequence.

The identification of one or more antibodies that bind(s) to KIR3DL2, particularly substantially or essentially the same epitope as monoclonal antibody 10G5 or 2B12, can be readily determined using any one of a variety of immunological screening assays in which antibody competition can be assessed. Many such assays are routinely practiced and are well known in the art (see, e.g., U.S. Pat. No. 5,660,827). It will be understood that actually determining the epitope to which an antibody described herein binds is not in any way required to identify an antibody that binds to the same or substantially the same epitope as the monoclonal antibody described herein. Any of a wide variety of assays can be used to assess binding of an antibody to human KIR3DL2. Protocols based upon ELISAs, radioimmunoassays, Western blotting, BIACORE, and other competition assays, inter alia, are suitable for use and are well known in the art.

For example, where the test antibodies to be examined are obtained from different source animals, or are even of a different Ig isotype, a simple competition assay may be employed in which the control (an antibody such as 10G5 or 2B12) and test antibodies are admixed (or pre-adsorbed) and applied to a sample containing KIR3DL2 polypeptides. Protocols based upon western blotting and the use of BIACORE analysis are suitable for use in such competition studies.

In certain embodiments, one pre-mixes the control antibodies (10G5 or 2B12) with varying amounts of the test antibodies (e.g., about 1:10 or about 1:100) for a period of time prior to applying to the KIR3DL2 antigen sample. In other embodiments, the control and varying amounts of test antibodies can simply be admixed during exposure to the KIR3DL2 antigen sample. As long as one can distinguish bound from free antibodies (e.g., by using separation or washing techniques to eliminate unbound antibodies) and (10G5 or 2B12 from the test antibodies (e.g., by using species-specific or isotype-specific secondary antibodies or by specifically labeling 10G5 or 2B12 with a detectable label) one can determine if the test antibodies reduce the binding of 10G5 or 2B12 to the antigens, indicating that the test antibody recognizes substantially the same epitope as 10G5 or 2B12. The binding of the (labeled) control antibodies in the absence of a completely irrelevant antibody can serve as the control high value. The control low value can be obtained by incubating the labeled (10G5 or 2B12) antibodies with unlabelled antibodies of exactly the same type (10G5 or 2B12), where competition would occur and reduce binding of the labeled antibodies. In a test assay, a significant reduction in labeled antibody reactivity in the presence of a test antibody is indicative of a test antibody that recognizes substantially the same epitope, and that "cross-reacts" or competes with the labeled (10G5 or 2B12) antibody. Any test antibody that reduces the binding of 10G5 or 2B12 to KIR3DL2 antigens by at least about 50%, such as at least about 60%, or more preferably at least about 80% or 90% (e.g., about 65-100%), at any ratio of 10G5 or 2B12:test antibody between about 1:10 and about 1:100 is considered to be an antibody that binds to substantially the same epitope or determinant as 10G5 or 2B12. Preferably, such test antibody will reduce the binding of 10F6 to the KIR3DL2 antigen by at least about 90% (e.g., about 95%).

Competition can also be assessed by, for example, a flow cytometry test. In such a test, cells bearing a given KIR3DL2 polypeptide can be incubated first with 10G5 or 2B12, for example, and then with the test antibody labeled with a fluorochrome or biotin. The antibody is said to compete with 10F6 if the binding obtained upon preincubation with a saturating amount of 10G5 or 2B12 is about 80%, preferably about 50%, about 40% or less (e.g., about 30%, 20% or 10%) of the binding (as measured by mean of fluorescence) obtained by the antibody without preincubation with 10G5 or 2B12. Alternatively, an antibody is said to compete with 10G5 or 2B12 if the binding obtained with a labeled 10G5 or 2B12 antibody (by a fluorochrome or biotin) on cells preincubated with a saturating amount of test antibody is about 80%, preferably about 50%, about 40%, or less (e.g., about 30%, 20% or 10%) of the binding obtained without preincubation with the test antibody.

A simple competition assay in which a test antibody is pre-adsorbed and applied at saturating concentration to a surface onto which a KIR3DL2 antigen is immobilized may also be employed. The surface in the simple competition assay is preferably a BIACORE chip (or other media suitable for surface plasmon resonance analysis). The control antibody (e.g., 10G5 or 2B12) is then brought into contact with the surface at a KIR3DL2-saturating concentration and the KIR3DL2 and surface binding of the control antibody is measured. This binding of the control antibody is compared with the binding of the control antibody to the KIR3DL2-containing surface in the absence of test antibody. In a test assay, a significant reduction in binding of the KIR3DL2-containing surface by the control antibody in the presence of a test antibody indicates that the test antibody recognizes substantially the same epitope as the control antibody such that the test antibody "cross-reacts" with the control antibody. Any test antibody that reduces the binding of control (such as 10G5 or 2B12) antibody to a KIR3DL2 antigen by at least about 30% or more, preferably about 40%, can be considered to be an antibody that binds to substantially the same epitope or determinant as a control (e.g., 10G5 or 2B12). Preferably, such a test antibody will reduce the binding of the control antibody (e.g., 10G5 or 2B12) to the KIR3DL2 antigen by at least about 50% (e.g., at least about 60%, at least about 70%, or more). It will be appreciated that the order of control and test antibodies can be reversed: that is, the control antibody can be first bound to the surface and the test antibody is brought into contact with the surface thereafter in a competition assay. Preferably, the antibody having higher affinity for the KIR3DL2 antigen is bound to the surface first, as it will be expected that the decrease in binding seen for the second antibody (assuming the antibodies are cross-reacting) will be of greater magnitude. Further examples of such assays are provided in, e.g., Saunal (1995) J. Immunol. Methods 183: 33-41, the disclosure of which is incorporated herein by reference.

Preferably, monoclonal antibodies that recognize a KIR3DL2 epitope will react with an epitope that is present on a substantial percentage of or even all relevant cells, e.g., malignant CD4+ T cells, cells from a SS or MF patient, but will not significantly react with other cells, i.e., cells that do not express KIR3DL2. In one aspect, the anti-KIR3DL2 antibodies bind KIR3DL2 but do not bind KIR3DL1 and/or KIR3DS1.

In some embodiments, the antibodies will bind to KIR3DL2-expressing cells from an individual or individuals with a disease characterized by expression of KIR3DL2-positive cells, i.e. an individual that is a candidate for treatment with one of the herein-described methods using an anti-KIR3DL2 antibody. Accordingly, once an antibody that specifically recognizes KIR3DL2 on cells is obtained, it can be tested for its ability to bind to KIR3DL2-positive cells (e.g. malignant CD4+ T cells) taken from a patient with a disorder such as SS or MF. In particular, prior to treating a patient with one of the present antibodies, it will be beneficial to test the ability of the antibody to bind malignant cells taken from the patient, e.g. in a blood sample, to maximize the likelihood that the therapy will be beneficial in the patient.

In one embodiment, the antibodies are validated in an immunoassay to test their ability to bind to KIR3DL2-expressing cells, e.g. malignant CD4+ T cells, pro-inflammatory CD4+ cells. For example, peripheral blood lymphocytes (PBLs) are taken from a plurality of patients, and CD4+ T cells are enriched from the PBLs, e.g., by flow cytometry using relevant antibodies (for malignant CD4+ cells see, e.g., Bagot et al. (2001) Blood 97:1388-1391, the disclosure of which is incorporated herein by reference), or CD4+CD28-cell fractions are isolated by magnetic separation on a MACS column (Miltenyi Biotec). The ability of a given antibody to bind to the cells is then assessed using standard methods well known to those in the art. Antibodies that are found to bind to a substantial proportion (e.g., 20%, 30%, 40%, 50%, 60%, 70%, 80% or more) of cells known to express KIR3DL2, e.g. T cells, from a significant percentage of individuals or patients (e.g., 5%, 10%, 20%, 30%, 40%, 50% or more) are suitable for use herein, both for diagnostic purposes to determine the presence or level of malignant T cells in a patient or for use in the herein-described therapeutic methods, e.g., for use to increase or decrease malignant T cell number or activity. To assess the binding of the antibodies to the cells, the antibodies can either be directly or indirectly labeled. When indirectly labeled, a secondary, labeled antibody is typically added. The binding of the antibodies to the cells can then be detected using, e.g., cytofluorometric analysis (e.g. FACScan). Such methods are well known to those of skill in the art.

Determination of whether an antibody binds within an epitope region can be carried out in ways known to the person skilled in the art. As one example of such mapping/characterization methods, an epitope region for an anti-KIR3DL2 antibody may be determined by epitope "footprinting" using chemical modification of the exposed amines/carboxyls in the KIR3DL2 protein. See, e.g., Ehring H, Analytical Biochemistry, Vol. 267 (2) pp. 252-259 (1999) Engen, J. R. and Smith, D. L. (2001) Anal. Chem. 73, 256A-265A. Another example of a suitable epitope identification technique is nuclear magnetic resonance epitope mapping (NMR). See, e.g., Ernst Schering Res Found Workshop. 2004; (44): 149-67; Huang et al. Journal of Molecular Biology, Vol. 281 (1) pp. 61-67 (1998); and Saito and Patterson, Methods. 1996 June; 9 (3): 516-24. Epitope mapping/characterization also can be performed using mass spectrometry methods. See, e.g., Downard, J Mass Spectrom. 2000 April; 35 (4): 493-503 and Kiselar and Downard, Anal Chem. 1999 May 1; 71 (9): 1792-801. Site-directed mutagenesis is another technique useful for elucidation of a binding epitope. For example, in "alanine-scanning", each residue within a protein segment is re-placed with an alanine residue, and the consequences for binding affinity measured. See, e.g., Clackson and Wells, Science 1995; 267:383-386; and Wells, Proc Natl Acad Sci USA 1996; 93:1-6. Other forms of "label-free" assay for epitope evaluation include surface plasmon resonance (SPR, BIACORE) and reflectometric interference spectroscopy (RifS). See, e.g., Fägerstam et al., Journal Of Molecular Recognition 1990; 3:208-14; Nice et al., J. Chromatogr. 1993; 646:159-168; Leipert et al., Angew. Chem. Int. Ed. 1998; 37:3308-3311; Kroger et al., Biosensors and Bioelectronics 2002; 17:937-944.

It should also be noted that an antibody binding the same or substantially the same epitope as an antibody described herein can be identified in one or more of the exemplary competition assays or assays for binding to KIR3DL2 mutant polypeptides described in PCT application number PCT/EP2013/069302 filed 17 Sep. 2013. Binding of anti-KIR3DL2 antibody to cells transfected with the KIR3DL2 mutants is measured and compared to the ability of anti-KIR3DL2 antibody to bind wild-type KIR3DL2 polypeptide (SEQ ID NO:1). A reduction in binding between an anti-KIR3DL2 antibody and a mutant KIR3DL2 polypeptide as used herein means that there is a reduction in binding affinity (e.g., as measured by known methods such as FACS testing of cells expressing a particular mutant, or by Biacore testing of binding to mutant polypeptides) and/or a reduction in the total binding capacity of the anti-KIR3DL2 antibody (e.g., as evidenced by a decrease in Bmax in a plot of anti-KIR3DL2 antibody concentration versus polypeptide concentration). A significant reduction in binding indicates that the mutated residue is directly involved in binding to the anti-KIR3DL2 antibody or is in close proximity to the binding protein when the anti-KIR3DL2 antibody is bound to KIR3DL2. An antibody epitope will thus preferably include such residue and may include additional residues adjacent to such residue.

Typically, an anti-KIR3DL2 antibody herein has an affinity for a KIR3DL2 polypeptide in the range of about $10^4$ to about $10^{11}$ $M^{-1}$ (e.g., about $10^8$ to about $10^{10}$ $M^{-1}$). For example, an antibody can have an average disassociation constant ($K_d$) of less than $1\times10^{-9}$ M with respect to KIR3DL2, as determined by, e.g., surface plasmon resonance (SPR) screening (such as by analysis with a BIAcore™ SPR analytical device). In a more particular exemplary aspect, an antibody can have a $K_d$ of about $1\times10^{-8}$ M to about $1\times10^{-10}$ M, or about $1\times10^{-9}$ M to about $1\times10^{-11}$ M, for KIR3DL2.

Antibodies can be characterized for example by a mean Kd of no more than about (i.e. better affinity than) 100, 60, 10, 5, or 1 nanomolar. Kd can be determined for example by immobilizing recombinantly produced human KIR3DL2 proteins on a chip surface, followed by application of the antibody to be tested in solution.

Once an antigen-binding compound is obtained it will generally be assessed for internalization (an antibody will preferably not internalize) into KIR3DL2-expressing target cells, and/or the ability to cause KIR3DL2 internalization into KIR3DL2-expressing target cells, to induce ADCC or CDC towards, inhibit the proinflammatory activity and/or proliferation of and/or cause the elimination of KIR3DL2-expressing target cells. Assessing the antigen-binding compound's ability to internalize or to induce ADCC, CDC or generally lead to the elimination or inhibition of activity of KIR3DL2-expressing target cells, can be carried out at any suitable stage of the method, e.g. as in the examples that are provided herein. This assessment can be useful at one or more of the various steps involved in the identification, production and/or development of an antibody (or other compound) destined for therapeutic use.

As used herein, an anti-KIR3DL2 antibody that is not "internalized" or that does not "internalize" is one that is not substantially taken up by (i.e., enters) the cell upon binding to KIR3DL2 on a mammalian cell (i.e. cell surface KIR3DL2). The non-internalizing antibody will of course include antibody fragments, human or humanized antibody and antibody conjugate.

Whether an anti-KIR3DL2 antibody internalizes upon binding KIR3DL2 on a mammalian cell, or whether a KIR3DL2 polypeptide undergoes intracellular internalization (e.g. upon being bound by an antibody) can be determined by various assays including those described in the experimental examples described in PCT application number PCT/EP2013/069302 filed 17 Sep. 2013, the disclosure of which is incorporated herein by reference.

Testing ADCC typically involves assessing cell-mediated cytotoxicity in which a KIR3DL2-expressing target cell (e.g. a Cou-L cell, Sezary Syndrome cell or any cell made to express at its surface KIR3DL2) with bound anti-KIR3DL2 antibody is recognized by an effector cell bearing Fc receptors, without the involvement of complement. A cell which does not express a KIR3DL2 antigen can optionally be used as a control. Activation of NK cell cytotoxicity is assessed by measuring an increase in cytokine production (e.g. IFN-γ production) or cytotoxicity markers (e.g. CD107 mobilization). Preferably the antibody will induce an increase in cytokine production, expression of cytotoxicity markers, or target cell lysis of at least 20%, 50%, 80%, 100%, 200% or 500% in the presence of target cells, compared to a control antibody (e.g. an antibody not binding to KIR3DL2, a KIR3DL2 antibody having murine constant regions). In another example, lysis of target cells is detected, e.g. in a chromium release assay, preferably the antibody will induce lysis of at least 10%, 20%, 30%, 40% or 50% of target cells. Where an antigen-binding compound is tested for both its ability to (a) induce both ADCC and (b) internalize into KIR3DL2-expressing cells and/or induce KIR3DL2 internalization, the assays can be carried out in any order.

In other embodiments, the antibodies are tested for their ability to interfere with binding of an HLA ligand of KIR3DL2 (e.g. B27dimer ($B27_2$) tetramer) to a KIR3DL2 polypeptide. See, e.g., assays described in PCT application number PCT/EP2013/069302.

Pharmaceutical Formulations

In one aspect, an agent according to the invention for use as a pharmaceutical, is provided. In one aspect, an agent according to the invention for use as a pharmaceutical in the treatment of malignant neoplasms, an inflammatory disorder, or an autoimmune disease, is provided.

In one aspect, an agent according to the invention for use as a pharmaceutical for eliminating or depleting KIR3DL2-expressing cells in a human patient, is provided.

In one embodiment, the present invention provides pharmaceutical composition comprising antibodies as described herein together with one or more carriers.

Accordingly, one object of the invention is to provide a pharmaceutical formulation comprising such an antibody which is present in a concentration from 1 mg/ml to 500 mg/ml, and wherein said formulation has a pH from 2.0 to 10.0. The formulation may further comprise a buffer system, preservative(s), tonicity agent(s), chelating agent(s), stabilizers and surfactants. In one embodiment, the pharmaceutical formulation is an aqueous formulation, i.e., formulation comprising water. Such formulation is typically a solution or a suspension. In a further embodiment, the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment, the pharmaceutical formulation is a freeze-dried formulation, whereto the physician or the patient adds solvents and/or diluents prior to use.

In another embodiment, the pharmaceutical formulation is a dried formulation (e.g. freeze-dried or spray-dried) ready for use without any prior dissolution.

In a further aspect, the pharmaceutical formulation comprises an aqueous solution of such an antibody, and a buffer, wherein the antibody is present in a concentration from 1 mg/ml or above, and wherein said formulation has a pH from about 6.0 to about 8.0.

In one embodiment, the pH of the formulation is at least about 6 and less than about 8 (and more generally less than about 7.7, 7.6, or 7.5) is used (e.g., in a range of 6-7.4, such as 6-7.4, such as 6-7, 6.2-7, 6.4-7.4, 6.5-7.5, 6.7-7.7, or about 7, about 7.4, etc.).

In a further embodiment, the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, sodium citrate, sodium borate, tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of the invention.

In a further embodiment, the formulation further comprises a pharmaceutically acceptable preservative. The preservative may be selected from, e.g., the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof. The preservative may, e.g., be present in a concentration from 0.1 mg/ml to 20 mg/ml, from 0.1 mg/ml to 5 mg/ml, from 5 mg/ml to 10 mg/ml, or from 10 mg/ml to 20 mg/ml. Each one of these specific preservatives constitutes an alternative embodiment of the invention. The use of a preservative in pharmaceutical compositions is well-known to the skilled person. For convenience reference is made to Remington: *The Science and Practice of Pharmacy*, 19$^{th}$ edition, 1995.

In a further embodiment, the formulation further comprises an isotonic agent. The isotonic agent may be, e.g., selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment, the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In one embodiment, the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. The sugar or sugar alcohol concentration can, e.g., be between about 1 mg/ml and about 150 mg/ml. The isotonic agent can be present in a concentration from, e.g., 1 mg/ml to 50 mg/ml, from 1 mg/ml to 7 mg/ml, from 8 mg/ml to 24 mg/ml, or from 25 mg/ml to 50 mg/ml. Each one of these specific isotonic agents constitutes an alternative embodiment of the invention. The use of an isotonic agent in pharmaceutical compositions is well-known to the skilled person. For convenience reference is made to Remington: *The Science and Practice of Pharmacy*, 19$^{th}$ edition, 1995.

In a further embodiment, the formulation also comprises a chelating agent. The chelating agent can, for example, be selected from salts of ethylenediaminetetraacetic acid (EDTA), citric acid, and aspartic acid, and mixtures thereof. The chelating agent may, for example, be present in a concentration from 0.1 mg/ml to 5 mg/ml, from 0.1 mg/ml to 2 mg/ml, or from 2 mg/ml to 5 mg/ml. Each one of these specific chelating agents constitutes an alternative embodiment of the invention. The use of a chelating agent in pharmaceutical compositions is well-known to the skilled person. For convenience reference is made to Remington: *The Science and Practice of Pharmacy*, 19th edition, 1995.

The formulation may or may not comprise a stabilizer. The use of a stabilizer in pharmaceutical compositions is well-known to the skilled person. For convenience reference is made to Remington: The Science and Practice of Pharmacy, 19th edition, 1995. More particularly, compositions of the invention can be stabilized liquid pharmaceutical compositions whose therapeutically active components include a polypeptide that possibly exhibits aggregate formation during storage in liquid pharmaceutical formulations. By "aggregate formation" is intended a physical interaction between the polypeptide molecules that results in formation of oligomers, which may remain soluble, or large visible aggregates that precipitate from the solution. By "during storage" is intended a liquid pharmaceutical composition or formulation once prepared, is not immediately administered to a subject. Rather, following preparation, it is packaged for storage, either in a liquid form, in a frozen state, or in a dried form for later reconstitution into a liquid form or other form suitable for administration to a subject. By "dried form" is intended the liquid pharmaceutical composition or formulation is dried either by freeze drying (i.e., lyophilization), spray drying, or air drying. Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

The pharmaceutical compositions of the invention may or may not further comprise an amount of an amino acid base sufficient to decrease aggregate formation by the polypeptide during storage of the composition. By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. In one embodiment, amino acids to use in preparing the compositions of the invention are those carrying a charged side chain, such as arginine, lysine, aspartic acid, and glutamic acid. Any stereoisomer (i.e., L, D, or a mixture thereof) of a particular amino acid (e.g. methionine, histidine, imidazole, arginine, lysine, isoleucine, aspartic acid, tryptophan, threonine and mixtures thereof) or combinations of these stereoisomers, may be present in the pharmaceutical compositions of the invention so long as the particular amino acid is present either in its free base form or its salt form. In one embodiment the L-stereoisomer is used. Compositions of the invention may also be formulated with analogues of these amino acids.

In a further embodiment of the invention methionine (or other sulphuric amino acids or amino acid analogous) may be added to inhibit oxidation of methionine residues to methionine sulfoxide when the polypeptide acting as the therapeutic agent is a polypeptide comprising at least one methionine residue susceptible to such oxidation. By "inhibit" is intended minimal accumulation of methionine oxidized species over time. Inhibiting methionine oxidation results in greater retention of the polypeptide in its proper molecular form. Any stereoisomer of methionine (L or D) or combinations thereof can be used. The amount to be added should be an amount sufficient to inhibit oxidation of the methionine residues such that the amount of methionine sulfoxide is acceptable to regulatory agencies. Typically, this means that the composition contains no more than about 10% to about 30% methionine sulfoxide. Generally, this can be achieved by adding methionine such that the ratio of methionine added to methionine residues ranges from about 1:1 to about 1000:1, such as 10:1 to about 100:1.

In a further embodiment, the formulation further comprises a stabilizer selected from the group of high molecular weight polymers or low molecular compounds. In a further embodiment of the invention the stabilizer is selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). Each one of these specific stabilizers constitutes an alternative embodiment of the invention.

The pharmaceutical compositions may also comprise additional stabilizing agents, which further enhance stability of a therapeutically active polypeptide therein. Stabilizing agents of particular interest to the present invention include, but are not limited to, methionine and EDTA, which protect the polypeptide against methionine oxidation, and a non-ionic surfactant, which protects the polypeptide against aggregation associated with freeze-thawing or mechanical shearing. In a further embodiment, the formulation further comprises a surfactant. The surfactant may, for example, be selected from a detergent, ethoxylated castor oil, polyglycolyzed glycerides, acetylated monoglycerides, sorbitan fatty acid esters, polyoxypropylene-polyoxyethylene block polymers (eg. poloxamers such as Pluronic® F68, poloxamer 188 and 407, Triton X-100), polyoxyethylene sorbitan fatty acid esters, polyoxyethylene and polyethylene derivatives such as alkylated and alkoxylated derivatives (tweens, e.g. Tween-20, Tween-40, Tween-80 and Brij-35), monoglycerides or ethoxylated derivatives thereof, diglycerides or polyoxyethylene derivatives thereof, alcohols, glycerol, lectins and phospholipids (eg. phosphatidyl serine, phosphatidyl choline, phosphatidyl ethanolamine, phosphatidyl inositol, diphosphatidyl glycerol and sphingomyelin), derivates of phospholipids (eg. dipalmitoyl phosphatidic acid) and lysophospholipids (eg. palmitoyl lysophosphatidyl-L-serine and 1-acyl-sn-glycero-3-phosphate esters of ethanolamine, choline, serine or threonine) and alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, and glycerophospholipids (eg. cephalins), glyceroglycolipids (eg. galactopyransoide), sphingoglycolipids (eg. ceramides, gangliosides), dodecylphosphocholine, hen egg lysolecithin, fusidic acid derivatives- (e.g. sodium tauro-dihydrofusidate etc.), long-chain fatty acids and salts thereof C6-C12 (eg. oleic acid and caprylic acid), acylcarnitines and derivatives, N$^\alpha$-acylated derivatives of lysine, arginine or histidine, or side-chain acylated derivatives of lysine or arginine, N$^\alpha$-acylated derivatives of dipeptides comprising any combination of lysine, arginine or histidine and a neutral or acidic amino acid, N$^\alpha$-acylated derivative of a tripeptide comprising any combination of a neutral amino acid and two charged amino acids, DSS (docusate sodium, CAS registry no [577-11-7]), docusate calcium, CAS registry no [128-49-4]), docusate potassium, CAS registry no [7491-09-0]), SDS (sodium dodecyl sulphate or sodium lauryl sulphate), sodium caprylate, cholic acid or derivatives thereof, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, zwitterionic surfactants (e.g. N-alkyl-N,N-dimethylammonio-1-propanesulfonates, 3-cholamido-1-propyldimethylammonio-1-propane-sulfonate, cationic surfactants (quaternary ammonium bases) (e.g. cetyl-trimethylammonium bromide, cetylpyridinium chloride), non-ionic surfactants (eg. Dodecyl β-D-glucopyranoside), poloxamines (eg. Tetronic's), which are tetrafunctional block copolymers derived from sequential addition of propylene oxide and ethylene oxide to ethylenediamine, or the surfactant may be selected from the group of imidazoline derivatives, or mixtures thereof. Each one of these specific surfactants constitutes an alternative embodiment of the invention.

In a further embodiment, the formulation further comprises protease inhibitors such as EDTA (ethylenediamine tetraacetic acid) and benzamidineHCl, but other commercially available protease inhibitors may also be used. The use of a protease inhibitor is particularly useful in pharmaceutical compositions comprising zymogens of proteases in order to inhibit autocatalysis. It is possible that other ingredients may be present in the peptide pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention. Pharmaceutical compositions containing an antibody according to the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Administration of pharmaceutical compositions according to the invention may be through any of several routes of administration, for example, subcutaneous, intramuscular, intraperitoneal, intravenous, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions of the current invention may be administered in any of several dosage forms, for example, as solutions, suspensions, emulsions, microemulsions, multiple emulsion, foams, salves, pastes, plasters, ointments, tablets, coated tablets, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants. The stability of a formulation according to any of the aspects described herein can, inter alia, be characterized on the basis of the lack of high molecular weight impurities (e.g., impurities that suggest aggregation (multimers) of antibody molecules in the formulation). In one aspect, a formulation according to the invention can be characterized as having a high molecular weight (HMW) impurity content of less than about 10% (such as about 5% or less) for at least one day, such as at least about one week, such as at least about 2 weeks, at least about 1 month, at least about 2 months, or even at least about 3 months of storage at about 5° C.

In one embodiment of the invention the pharmaceutical formulation comprising the antibody is stable for more than 1 year, optionally 2 years of storage, optionally 3 years of storage. In another embodiment of the invention the pharmaceutical formulation comprising the antibody is stable for more than 4 weeks of usage and for more than 3 years of storage. In a further embodiment of the invention the pharmaceutical formulation comprising the antibody is stable for more than 4 weeks of usage and for more than two years of storage. In an even further embodiment of the invention the pharmaceutical formulation comprising the antibody is stable for more than 2 weeks of usage and for more than two years of storage.

In one aspect, the invention provides a formulation comprising sodium chloride as a tonicity modifier.

In one embodiment, the invention provides a formulation in which a sodium phosphate or a sodium citrate (base) buffer is incorporated in the formulation.

In one embodiment, the invention provides a formulation in which a polysorbate 80 is incorporated in the formulation as surfactant.

A formulation according to any of the aspects of the invention can have any suitable concentration of the antibody. Typically, the concentration is about 0.05 mg/mL to about 10 mg/mL (e.g., about 1 mg/mL to about 5 mg/mL). In one exemplary aspect, the formulation is provided as a relatively concentrated antibody formulation, which may be, e.g., a formulation that is to be diluted prior to administration (typically by intravenous administration or direct parenteral injection) having a concentration of about 10 mg/mL. In another exemplary aspect, the formulation is provided as a relatively dilute formulation, such as a formulation that is infusion/injection-ready, wherein the concentration of the antibody in the formulation is about 0.05 mg/mL or about 0.1 mg/mL.

In one aspect, the formulation has an antibody concentration of about 1 mg/mL.

In an exemplary aspect, the invention provides a pharmaceutically acceptable and active formulation prepared from a mixture of ingredients comprising (a) an amount of an IgG antibody molecule of the disclosure such that the concentration of antibody in the formulation is between about 0.5 mg/mL and about 10 mg/mL; (b) sodium phosphate (e.g., sodium phosphate dibasic/potassium phosphate monobasic), sodium citrate (e.g. sodium citrate/citric acid) or sodium borate (sodium borate/boric acid); (c) sodium chloride; and (e) polysorbate 80, wherein the formulation has a pH of between about 6.7 and 7.7, or about 7.4.

Further aspects and advantages will be disclosed in the following experimental section, which should be regarded as illustrative and not limiting the scope of this application.

EXAMPLES

Example 1—Generation of Humanized Anti-KIR3DL2 Antibodies by CDR Grafting

Anti-KIR3DL2 antibodies were obtained in PCT application number PCT/EP2013/069302 filed 17 Sep. 2013 as candidates for humanization.

Humanization was first carried by complementary determining region (CDR) grafting of heavy and light chains, followed by introduction of back-mutations. The mouse parental genes and the human genes used for modelling and design are listed in Table 1 below. Antibodies were produced using CHO cells.

TABLE 1

| Antibody | Species | Germinal genes of parental and humanized antibodies | | | |
|---|---|---|---|---|---|
| | | Light chain | | Heavy chain | |
| | | VK* | JK* | VH* | JH* |
| 10G5 | Mouse | IGKV12-46*01 | IGKJ2*01 | IGHV1-62-1*01 | IGHJ2*01 |
| | Human | IGKV1-NL1*01 | | IGHV1-46*03 | IGHJ6*01 |
| 2B12 | Mouse | IGKV6-25*01 | IGKJ1*01 | VHVGAM3.8.a6.115 # | IGHJ4*01 |
| | Human | IGKV4-1*01 | IGKJ4*01 | IGHV7-4-1*02 | IGHJ6*01 |
| | | IGKV1-39*01 | | IGHV1-c*01 | |

*IMGT name and nomenclature
This sequence refers to VHVGAM3.8.a6.115 germline gene in record AJ851868.
It is linked to Mus musculus IGHV12-1-1 in the IMGT database but the two sequences are not strictly identical Antibody 10G5

The humanized protein sequences of 10G5 light chains are aligned below. 10G5-LC is shown in SEQ ID NO: 34. IGKV1-NL1 is shown in SEQ ID NO: 35. Hum2C4 is shown in SEQ ID NO: 36. 3RKD is shown in SEQ ID NO: 37. CDRs are underlined in the 10G5-LC and back-mutations are underlined in the -L1 to -L5 variants.

```
10G5-LC    DIQMTQSPASLSVSVGETVTITCRASENIYSNLAWYQQKQGKSPQLLVYAATNLADGVPS

IGKV1-NL1  DIQMTQSPSSLSASVGDRVTITCRASQGISNSLAWYQQKPGKAPKLLLYAASRLESGVPS

10G5-L0    DIQMTQSPSSLSASVGDRVTITCRASENIYSNLAWYQQKPGKAPKLLLYAATNLADGVPS

10G5-L1    DIQMTQSPSSLSASVGDRVTITCRASENIYSNLAWYQQKPGKAPKLLVYAATNLADGVPS

10G5-L2    DIQMTQSPSSLSASVGDRVTITCRASENIYSNLAWYQQKPGKAPQLLVYAATNLADGVPS

10G5-L3    DIQMTQSPSSLSASVGDRVTITCRASENIYSNLAWYQQKPGKAPQLLVYAATNLADGVPS

10G5-L4    DIQMTQSPSSLSASVGDRVTITCRASENIYSNLAWYQQKQGKAPQLLVYAATNLADGVPS

10G5-L5    DIQMTQSPSSLSASVGETVTITCRASENIYSNLAWYQQKQGKAPQLLVYAATNLADGVPS

Hum 2C4:   DIQMTQSPSSLSASVGDRVTITCKASQDVSIGVAWYQQKPGKAPKLLIYSASYRYTGVPS

3RKD       DIQMTQSPASLSVSVGETVTITCRASEIIYSNLAWYQQKQGKSPQLLVYSATNLAEGVPS

10G5-LC    RFSGSGSGTQYSLKINSLQSEDFGSYYCQHFWGTPYTFGGGTKLEIK

IGKV1-NL1  RFSGSGSGTDYTLTISSLQPEDFATYYC-------------------

10G5-L0    RFSGSGSGTDYTLTISSLQPEDFATYYCQHFWGTPYTFGQGTKLEIK

10G5-L1    RFSGSGSGTDYTLTISSLQPEDFATYYCQHFWGTPYTFGQGTKLEIK

10G5-L2    RFSGSGSGTDYTLTISSLQPEDFATYYCQHFWGTPYTFGGGTKLEIK

10G5-L3    RFSGSGSGTQYTLTISSLQPEDFATYYCQHFWGTPYTFGGGTKLEIK

10G5-L4    RFSGSGSGTQYTLTINSLQPEDFATYYCQHFWGTPYTFGGGTKLEIK

10G5-L5    RFSGSGSGTQYTLTINSLQPEDFATYYCQHFWGTPYTFGGGTKLEIK

Hum 2C4:   RFSGSGSGTDFTLTISSLQPEDFATYYCQQYYIYPYTFGQGTKVEIK

3RKD       RFSGSGSGTQYSLKINSLQSEDFGSYYCQHFWGNPWTFGGGTKLEIK
```

The humanized antibody 2C4 (anti-ErbB2; pdb 1S78 and 1L7I) and the mouse antibody 8C11 (anti-Hepatitis E Virus capsid protein; pdb 3RKD) were used as a template for structural prospective assessment. The parental JK segment were kept unmodified as well as the Vernier zone residues of parental framework 2 (FW2) (including adjacent flanking residues). Therefore, the L2 light chain was used as a basic starting template for additional back mutations.

The four light chains L2, L3, L4 and L5 were finally chosen for antibody generation.

The humanized protein sequences of 10G5 heavy chains are aligned below. 10G5-HC is shown in SEQ ID NO: 38. IGHV1-46 is shown in SEQ ID NO: 39. 1i9r is shown in SEQ ID NO: 40. 1it9 is shown in SEQ ID NO: 41. 1E6O is shown in SEQ ID NO: 42. CDRs are underlined in the 10G5-HC sequence and back-mutations are underlined in the -H1 to -H6 variants.

```
10G5-HC    QVQLQQSAAELARPGASVKMSCKASGYTFTSYTMHWVKQRPGQGLEWIGYINPSSGYTEN

IGHV1-46   QVQLVQSGAEVKKPGASVKVSCKASGYTFTSYYMHWVRQAPGQGLEWMGIINPSGGSTSY

10G5-H0    QVQLVQSGAEVKKPGASVKVSCKASGYTFTSYTMHWVRQAPGQGLEWMGYINPSSGYTEN

10G5-H1    QVQLVQSGAEVKKPGASVKVSCKASGYTFTSYTMHWVRQAPGQGLEWMGYINPSSGYTEN

10G5-H2    QVQLVQSGAEVKKPGASVKVSCKASGYTFTSYTMHWVRQAPGQGLEWIGYINPSSGYTEN

10G5-H3    QVQLVQSGAEVKKPGASVKVSCKASGYTFTSYTMHWVRQAPGQGLEWIGYINPSSGYTEN

10G5-H4    QVQLQQSGAEVKKPGASVKMSCKASGYTFTSYTMHWVRQAPGQGLEWIGYINPSSGYTEN

10G5-H5    QVQLVQSGAELARPGASVKVSCKASGYTFTSYTMHWVRQAPGQGLEWIGYINPSSGYTEN

10G5-H6    QVQLQQSGAEVKKPGASVKMSCKASGYTFTSYTMHWVKQRPGQGLEWIGYINPSSGYTEN

1i9r       QVQLVQSGAEVVKPGASVKLSCKASGYIFTSYYMYWVKQAPGQGLEWIGEINPSNGDTNF

1it9       QVQLVQSGAEVKKPGASVKVSCKASGYTFTSYWMQWVKQAPGQGLEWMGEIDPSDSYTNY

1E6O       EVQLQQSGAELARPGASVKMSCKASGYTFTSYTMHWVKQRPGQGLEWIGYINPSSGYSNY

10G5-HC    NRKFKDKTTLTADKSSSTAYMQLSSLTSEDSAVYYCARLGKGLLPPFDYWGQGTTLTVSS

IGHV1-46   AQKFQGRVTMTRDTSTSTVYMELSSLRSEDTAVYYCAR----------------------

10G5-H0    NRKFKDRVTMTRDTSTSTVYMELSSLRSEDTAVYYCARLGKGLLPPFDYWGQGTTVTVSS

10G5-H1    NRKFKDKVTMTRDTSTSTVYMELSSLRSEDTAVYYCARLGKGLLPPFDYWGQGTTVTVSS

10G5-H2    NRKFKDKTTMTRDTSTSTVYMELSSLRSEDTAVYYCARLGKGLLPPFDYWGQGTTVTVSS

10G5-H3    NRKFKDKTTMTADTSTSTAYMELSSLRSEDTAVYYCARLGKGLLPPFDYWGQGTTVTVSS

10G5-H4    NRKFKDKTTLTADTSTSTAYMELSSLRSEDTAVYYCARLGKGLLPPFDYWGQGTTLTVSS

10G5-H5    NRKFKDKTTLTADKSTSTAYMELSSLRSEDTAVYYCARLGKGLLPPFDYWGQGTTVTVSS

10G5-H6    NRKFKDKTTLTADKSTSTAYMELSSLRSEDTAVYYCARLGKGLLPPFDYWGQGTTLTVSS

1i9r       NEKFKSKATLTVDKSASTAYMELSSLRSEDTAVYYCTRSDGRNDM**DSWGQGTLVTVSS

1it9       NQKFKGKATLTVDTSTSTAYMELSSLRSEDTAVYYCARNRDY--WYFDVWGEGTLVTVSS

1E6O       NQKFKDKATLTADKSSSTAYMQLSSLTSEDSAVYYCSRPVVRLGYNFDYWGQGSTLTVSS
```

The humanized anti-Fas antibody HFE7A (pdb 1IT9), the humanized anti-CD40-L antibody 5C8 (pdb 1I9R) and the mouse anti-HIV-1 capsid protein p24 antibody 13B5 (pdb 1E60) were used as templates for structural prospective assessment. Based on 3D structure examination, three of the five FW3 Vernier zone residues were kept unmodified. Vernier zone residues of FW2 were not modified either. Therefore, the H3 heavy chain was used as a basic starting template for additional back mutations. The four heavy chains H3, H4, H5 and H6 were chosen for antibody generation.

Antibody 2B12

Two human VK genes were used for CDR grafting by a mosaic approach. The FW1 came from IGKV1-39, and the FW2 and FW3 from IGKV4-1.

The humanized light chain protein sequences are aligned below. 2B12-LC is shown in SEQ ID NO: 43. IGKV1-39 is shown in SEQ ID NO: 44. IGKV4-1 is shown in SEQ ID NO: 45. 1NCA is shown in SEQ ID NO: 46. 1ZA6 is shown in SEQ ID NO: 47. 1PG7 is shown in SEQ ID NO: 48. 1b2w is shown in SEQ ID NO: 49. 1fvd is shown in SEQ ID NO: 50. 2fgw is shown in SEQ ID NO: 51. DRs are underlined in the 2B12-LC sequence and back-mutations are underlined in the -L0 to -L4 variants.

```
2B12-LC    DIVMTQSHKFMSTSLGDRVSFTCKASQDVSTAVAWYQQKPGQSPKLLIYWTSTRHTGVPD

IGKV1-39   DIQMTQSPSFLSASVGDRVTITCRASQSISSYLNWYQQKPGKAPKLLIYAASSLQSGVPS

IGKV4-1    DIVMTQSPDSLAVSLGERATINCKSSQSVL--LAWYQQKPGQPPKLLIYWASTRESGVPD

2B12-L0    DIQMTQSPSFLSASVGDRVTITCKASQDVSTAVAWYQQKPGQPPKLLIYWTSTRHTGVPD

2B12-L1    DIQMTQSPSFLSASVGDRVTITCKASQDVSTAVAWYQQKPGQPPKLLIYWTSTRHTGVPD

2B12-L2    DIVMTQSPSFLSASVGDRVTITCKASQDVSTAVAWYQQKPGQPPKLLIYWTSTRHTGVPD

2B12-L3    DIVMTQSPSFLSASVGDRVTFTCKASQDVSTAVAWYQQKPGQSPKLLIYWTSTRHTGVPD

2B12-L4    DIVMTQSHKFLSASVGDRVTFTCKASQDVSTAVAWYQQKPGQSPKLLIYWTSTRHTGVPD

1NCA       DIVMTQSPKFMSTSVGDRVTITCKASQDVSTAVVWYQQKPGQSPKLLIYWASTRHIGVPD

1ZA6       DIVMSQSPDSLAVSLGERVTLNCKSSQSLL*YLAWYQQKPGQSPKLLIYWASARESGVPD

1PG7       DIQMTQSPSSLSASVGDRVTITCRASRDIKSYLNWYQQKPGKAPKVLIYYATSLAEGVPS

1b2w       DIQMTQSPSTLSASVGDRVTITCKASENVDTYVSWYQQKPGKAPKLLIYGASNRYTGVPS

1fvd       DIQMTQSPSSLSASVGDRVTITCRASQDVNTAVAWYQQKPGKAPKLLIYSASFLESGVPS

2fgw       DIQMTQSPSSLSASVGDRVTITCRASQDINNYLNWYQQKPGKAPKLLIYYTSTLHSGVPS

2B12-LC    RFTGSGSGTDYTLTISSVQAEDLALYYCQQHYSTPWTFGGGTKLEIK

IGKV1-39   RFSGSGSGTDFTLTISSLQPEDFATYYC-------------------

IGKV4-1    RFSGSGSGTDFTLTISSLQAEDVAVYYC

2B12-L0    RFSGSGSGTDFTLTISSLQAEDVAVYYCQQHYSTPWTFGGGTKVEIK

2B12-L1    RFSGSGSGTDYTLTISSLQAEDVAVYYCQQHYSTPWTFGGGTKVEIK

2B12-L2    RFSGSGSGTDYTLTISSVQAEDVAVYYCQQHYSTPWTFGGGTKVEIK

2B12-L3    RFSGSGSGTDYTLTISSVQAEDVAVYYCQQHYSTPWTFGGGTKVEIK

2B12-L4    RFSGSGSGTDYTLTISSVQAEDVAVYYCQQHYSTPWTFGGGTKLEIK

1NCA       RFAGSGSGTDYTLTISSVQAEDLALYYCQQHYSPPWTFGGGTKLEIK

1ZA6       RFSGSGSGTDFTLTISSVQAEDVAVYYCQQYYSYPLTFGAGTKLELK

1PG7       RFSGSGSGTDYTLTISSLQPEDFATYYCLQHGESPWTFGQGTKVEIK

1b2w       RFSGSGSGTDFTLTISSLQPDDFATYYCGQSYNYPFTFGQGTKVEVK

1fvd       RFSGSRSGTDFTLTISSLQPEDFATYYCQQHYTTPPTFGQGTKVEIK

2fgw       RFSGSGSGTDYTLTISSLQPEDFATYYCQQGNTLPPTFGQGTKVEIK
```

The humanized anti-TAG-72 antibody CC49 (pdb 1ZA6), the humanized anti-tissue factor antibody D3H44 (pdb 1PG7), the humanized anti-p185HER2 antibody 4D5 (pdb 1FVD), a humanized anti-gamma interferon antibody (pdb 1B2W), a humanized anti-CD18 antibody (pdb 2FGW) and the mouse anti-neuraminidase from influenza virus subtype N9 antibody NC41 (pdb 1NCA) were used as templates for structural prospective assessment. The Vernier zone residues of FW3 were kept unmodified. Therefore, the L1 light chain was used as a basic starting template for additional back mutations. The four light chains L1, L2, L3 and L4 were finally chosen for antibody generation.

Two human VH genes were used for CDR grafting by a mosaic approach. The FW1 and FW3 came from IGHV7-4-1*02 and the FW2 from IGHV1-c*01.

The humanized heavy chain protein sequences are aligned below. 2B12-HC is shown in SEQ ID NO: 52. IGHV7 is shown in SEQ ID NO: 53. IGHV1-c is shown in SEQ ID NO: 54. 1BJ1-H is shown in SEQ ID NO: 55. 9046-H is shown in SEQ ID NO: 56. CDRs are underlined in the 2B12-HC sequence and back-mutations are underlined in the -H1 to -H4 variants.

2B12-HC QIQLVQSGPELKKPGETVRISCKASGYTFTTAGMQWVQKTPGKGLKWIGWINSHSGVPKY

IGHV7 QVQLVQSGSELKKPGASVKVSCKASGYTFTSYAMNWVRQAPGQGLEWMGWINTNTGNPTY

IGHV1-C QVQLVQSWAEVRKSGASVKVSCSFSGFTITSYGIHWVQQSPGQGLEWMGWINPGNGSPSY

2B12-H0 QVQLVQSGSELKKPGASVKVSCKASGYTFTTAGMQWVRQAPGQGLEWMGWINSHSGVPKY

2B12-H1 QVQLVQSGSELKKPGASVKVSCKASGYTFTTAGMQWVQKSPGQGLEWMGWINSHSGVPKY

2B12-H2 QIQLVQSGSELKKPGASVKVSCKASGYTFTTAGMQWVRQAPGQGLEWIGWINSHSGVPKY

2B12-H3 QIQLVQSGSELKKPGASVKVSCKASGYTFTTAGMQWVQKSPGQGLEWIGWINSHSGVPKY

2B12-H4 QIQLVQSGSELKKPGASVKVSCKASGYTFTTAGMQWVQKTPGKGLEWIGWINSHSGVPKY

1BJ1-H EVQLVESGGGLVQPGGSLRLSCAASGYTFTNYGMNWVRQAPGKGLEWVGWINTYTGEPTY

9046-H EVQLVQSGPGLVQPGGSVRISCAASGYTFTNYGMNWVKQAPGKGLEWMGWINTYTGESTY

2B12-HC AEDFKGRFAFSLETSASTAYLQISTLKNEDTATYFCARGGDEGVMDYWGQGTSVTVSS

IGHV7 AQGFTGRFVFSLDTSVSTAYLQISSLKAEDTAVYYCAR

IGHV1-C AKKFQGRFTMTRDMSTTTAYTDLSSLTSEDMAVYY---

2B12-H0 AEDFKGRFVFSLDTSVSTAYLQISSLKAEDTAVYYCARGGDEGVMDYWGQGTTVTVSS

2B12-H1 AEDFKGRFVFSLDTSVSTAYLQISSLKAEDTAVYFCARGGDEGVMDYWGQGTTVTVSS

2B12-H2 AEDFKGRFVFSLDTSVSTAYLQISSLKAEDTAVYFCARGGDEGVMDYWGQGTTVTVSS

2B12-H3 AEDFKGRFAFSLDTSVSTAYLQISSLKAEDTAVYFCARGGDEGVMDYWGQGTTVTVSS

2B12-H4 AEDFKGRFAFSLDTSASTAYLQISSLKAEDTAVYFCARGGDEGVMDYWGQGTSVTVSS

1BJ1-H AADFKRRFTFSLDTSKSTAYLQMNSLRAEDTAVYYCAKYP-HWYFDVWGQGTLVTVSS

9046-H ADSFKGRFTFSLDTSASAAYLQINSLRAEDTAVYYCARFAI**KGDYWGQGTLLTVSS

A humanized anti-VEGF neutralizing antibody (pdb 1BJ1), and the citatuzumab bogatox antibody (9046-H) were respectively used as templates for structural prospective assessment and primary sequence comparison. Based on 1BJ1 3D structure examination, the FW2 VH/VL interface residue Lys39 were kept unmodified as well as the FW3 Phe which is located just upstream of the last Cys. Therefore, the H1 heavy chain was used as a basic starting template for additional back mutations and generation of H3 and H4 variants. Alternatively, a variant which keeps the three FWs of IGHV7-4-1 was also included (H2).

The four 2B12 heavy chains H1, H2, H3 and H4 were finally chosen for antibody generation.

Amino acid sequences for 2B12 and 10G5 light and heavy chain variable regions produced are shown below (L indicates light chain, H indicates heavy chain).

```
10G5-L0:
                                            (SEQ ID NO: 8)
DIQMTQSPSSLSASVGDRVTITCRASENIYSNLAWYQQKPGKAPKLLLYA

ATNLADGVPSRFSGSGSGTDYTLTISSLQPEDFATYYCQHFWGTPYTFGQ

GTKLEIK

10G5-L2:
                                            (SEQ ID NO: 9)
DIQMTQSPSSLSASVGDRVTITCRASENIYSNLAWYQQKPGKAPQLLVYA

ATNLADGVPSRFSGSGSGTDYTLTISSLQPEDFATYYCQHFWGTPYTFGG

GTKLEIK

10G5-L3:
                                           (SEQ ID NO: 10)
DIQMTQSPSSLSASVGDRVTITCRASENIYSNLAWYQQKPGKAPQLLVYA

ATNLADGVPSRFSGSGSGTQYTLTISSLQPEDFATYYCQHFWGTPYTFGG

GTKLEIK

10G5-L4:
                                           (SEQ ID NO: 11)
DIQMTQSPSSLSASVGDRVTITCRASENIYSNLAWYQQKQGKAPQLLVYA

ATNLADGVPSRFSGSGSGTQYTLTINSLQPEDFATYYCQHFWGTPYTFGG

GTKLEIK

10G5-L5:
                                           (SEQ ID NO: 12)
DIQMTQSPSSLSASVGETVTITCRASENIYSNLAWYQQKQGKAPQLLVYA

ATNLADGVPSRFSGSGSGTQYTLTINSLQPEDFATYYCQHFWGTPYTFGG

GTKLEIK

10G5-H0:
                                           (SEQ ID NO: 13)
QVQLVQSGAEVKKPGASVKVSCKASGYTFTSYTMHWVRQAPGQGLEWMGY

INPSSGYTENNRKFKDRVTMTRDTSTSTVYMELSSLRSEDTAVYYCARLG

KGLLPPFDYWGQGTTVTVSS

10G5-H3:
                                           (SEQ ID NO: 14)
QVQLVQSGAEVKKPGASVKVSCKASGYTFTSYTMHWVRQAPGQGLEWIGY

INPSSGYTENNRKFKDKTTMTADTSTSTAYMELSSLRSEDTAVYYCARLG

KGLLPPFDYWGQGTTVTVSS

10G5-H4:
                                           (SEQ ID NO: 15)
QVQLQQSGAEVKKPGASVKMSCKASGYTFTSYTMHWVRQAPGQGLEWIGY

INPSSGYTENNRKFKDKTTLTADTSTSTAYMELSSLRSEDTAVYYCARLG

KGLLPPFDYWGQGTTLTVSS

10G5-H5:
                                           (SEQ ID NO: 16)
QVQLVQSGAELARPGASVKVSCKASGYTFTSYTMHWVRQAPGQGLEWIGY

INPSSGYTENNRKFKDKTTLTADKSTSTAYMELSSLRSEDTAVYYCARLG

KGLLPPFDYWGQGTTVTVSS

10G5-H6:
                                           (SEQ ID NO: 17)
QVQLQQSGAEVKKPGASVKMSCKASGYTFTSYTMHWVKQRPGQGLEWIGY

INPSSGYTENNRKFKDKTTLTADKSTSTAYMELSSLRSEDTAVYYCARLG

KGLLPPFDYWGQGTTLTVSS

2B12-L0:
                                           (SEQ ID NO: 24)
DIQMTQSPSFLSASVGDRVTITCKASQDVSTAVAWYQQKPGQPPKLLIYW

TSTRHTGVPDRFSGSGSGTDFTLTISSLQAEDVAVYYCQQHYSTPWFGGG

TKVEIK

2B12-L1:
                                           (SEQ ID NO: 25)
DIQMTQSPSFLSASVGDRVTITCKASQDVSTAVAWYQQKPGQPPKLLIYW

TSTRHTGVPDRFSGSGSGTDYTLTISSLQAEDVAVYYCQQHYSTPWTFGG

GTKVEIK

2B12-L2:
                                           (SEQ ID NO: 26)
DIVMTQSPSFLSASVGDRVTITCKASQDVSTAVAWYQQKPGQPPKLLIYW

TSTRHTGVPDRFSGSGSGTDYTLTISSVQAEDVAVYYCQQHYSTPWTFGG

GTKVEIK

2B12-L3:
                                           (SEQ ID NO: 27)
DIVMTQSPSFLSASVGDRVTFTCKASQDVSTAVAWYQQKPGQSPKLLIYW

TSTRHTGVPDRFSGSGSGTDYTLTISSVQAEDVAVYYCQQHYSTPWTFGG

GTKVEIK

2B12-L4:
                                           (SEQ ID NO: 28)
DIVMTQSHKFLSASVGDRVTFTCKASQDVSTAVAWYQQKPGQSPKLLIYW

TSTRHTGVPDRFSGSGSGTDYTLTISSVQAEDVAVYYCQQHYSTPWTFGG

GTKLEIK

2B12-H0:
                                           (SEQ ID NO: 29)
QVQLVQSGSELKKPGASVKVSCKASGYTFTTAGMQWVRQAPGQGLEWMGW

INSHSGVPKYAEDFKGRFVFSLDTSVSTAYLQISSLKAEDTAVYYCARGG

DEGVMDYWGQGTTVTVSS

2B12-H1:
                                           (SEQ ID NO: 30)
QVQLVQSGSELKKPGASVKVSCKASGYTFTTAGMQWVQKSPGQGLEWMGW

INSHSGVPKYAEDFKGRFVFSLDTSVSTAYLQISSLKAEDTAVYFCARGG

DEGVMDYWGQGTTVTVSS
```

-continued

2B12-H2:
(SEQ ID NO: 31)
QIQLVQSGSELKKPGASVKVSCKASGYTFTTAGMQWVRQAPGQGLEWIGW

INSHSGVPKYAEDFKGRFVFSLDTSVSTAYLQISSLKAEDTAVYFCARGG

DEGVMDYWGQGTTVTVSS

2B12-H3:
(SEQ ID NO: 32)
QIQLVQSGSELKKPGASVKVSCKASGYTFTTAGMQWVQKSPGQGLEWIGW

INSHSGVPKYAEDFKGRFAFSLDTSVSTAYLQISSLKAEDTAVYFCARGG

DEGVMDYWGQGTTVTVSS

2B12-H4:
(SEQ ID NO: 33)
QIQLVQSGSELKKPGASVKVSCKASGYTFTTAGMQWVQKTPGKGLEWIGW

INSHSGVPKYAEDFKGRFAFSLDTSASTAYLQISSLKAEDTAVYFCARGG

DEGVMDYWGQGTSVTVSS

Sixteen humanized variants of each of antibodies 2B12 and 10G5 were constructed that contained the different back mutations (the amino acid of murine origin in place of human framework residues) compared to the parental chimeric version. All the antibody variants were successfully produced in CHO cells as human IgG1 antibodies, in combinations shown below in Tables 2 and 3.

TABLE 2

Combinatorial co-transfection for M-K323-10G5 antibody variants

|  | 10G5-L2 | 10G5-L3 | 10G5-L4 | 10G5-L5 | 10G5-LParental |
|---|---|---|---|---|---|
| 10G5-H3 | 10G5-H3L2 | 10G5-H3L3 | 10G5-H3L4 | 10G5-H3L5 | |
| 10G5-H4 | 10G5-H4L2 | 10G5-H4L3 | 10G5-H4L4 | 10G5-H4L5 | |
| 10G5-H5 | 10G5-H5L2 | 10G5-H5L3 | 10G5-H5L4 | 10G5-H5L5 | |
| 10G5-H6 | 10G5-H6L2 | 10G5-H6L3 | 10G5-H6L4 | 10G5-H6L5 | |
| 10G5-HParental | | | | | 10G5-H/LParental |

TABLE 3

Combinatorial co-transfection for M-K323-2B12 antibody variants

|  | 2B12-L1 | 2B12-L2 | 2B12-L3 | 2B12-L4 | 2B12-LParental |
|---|---|---|---|---|---|
| 2B12-H1 | 2B12-H1L1 | 2B12-H1L2 | 2B12-H1L3 | 2B12-H1L4 | |
| 2B12-H2 | 2B12-H2L1 | 2B12-H2L2 | 2B12-H2L3 | 2B12-H2L4 | |
| 2B12-H3 | 2B12-H3L1 | 2B12-H3L2 | 2B12-H3L3 | 2B12-H3L4 | |
| 2B12-H4 | 2B12-H4L1 | 2B12-H4L2 | 2B12-H4L3 | 2B12-H4L4 | |
| 2B12-HParental | | | | | 2B12-H/LParental |

Antibody variants were purified and analysed by flow cytometry titration using KIR3DL2 positive cell lines. Briefly, RAJI-KIR3DL2 cell line was counted in trypan blue. Cells were adjusted at 1 million per ml. 100W of the previous suspension was transferred in 96W-U bottom microplate (100 000 cells per well). Cells were washed 1× with 100W/well of Staining Buffer (SB), and spun down for 2 min at 400 g. Dilution ranges at ⅓ were performed from 100 µg/ml to 2.10-3 µg/ml for each purified antibody. 50µl of each dilution was added to each well. Cells were incubated for 1H at 4° C. Cells were washed 3× in SB (100W) and spun down for 2 min at 400 g. Goat anti-human-PE (Fc spe) diluted at 1/200 was added to the plate and cells were incubated for 30 min at 4° C. Cells were washed 2× and immediately analyzed on FACS CANTO cytometer. All the supernatants were positive in that assay, indicating that all the humanized variants retain binding to the target antigen.

For 2B12 and 10G5 antibodies, it appeared that all the variants bind equally well to the target cells as parental chimeric versions and are undistinguishable from one another and from the chimeric antibodies in that assay.

By way of comparison, for another anti-KIR3DL2 antibody that was humanized, a global loss of affinity was observed. For some variants of this clone, H4L1, H4L2 and H4L3 for instance, the re-introduction of murine residues into the human framework sequences (back-mutation) slightly improved the apparent binding to cell surface antigens but did not restore a full binding activity.

Example 2—Identification of Humanized Anti-KIR3DL2 Antibodies with Decreased Aggregation Propensity The aggregation propensity of humanized variants of 2B12 and 10G5 produced in the human IgG1 format was studied with respect to the pH of their formulation. For each mAb, the aggregation propensity assays required about 1 mg of purified material.

The following Monoclonal Antibodies (mAbs) were studied: 2B12-H1L1; 2B12-H1L2; 2B12-H2L1; 2B12-H2L2; 10G5-H3L2; and 10G5-H4L2.

The aggregation propensity of these mAbs was evaluated as a function of their formulation pH. A total of five pharmaceutically acceptable buffer solutions ranging from pH 5.5 to 8 were selected; therefore, each mAb was prepared in five formulations at a final concentration of 1 mg/mL as shown in Tables 4-8.

TABLE 4 pH = 5.5 Formulation

| Ingredients | Function | Quantity/Concentration |
|---|---|---|
| mAb | Active | 1 mg/mL |
| Sodium citrate/Citric acid | Buffer | 10 mM |
| NaCl | Isotonic agent | 9 mg/mL |
| Polysorbate 80 | Surfactant | 0.1 mg/mL |
| Water for injection | Diluent | Qs. |

TABLE 5 pH = 6.5 Formulation

| Ingredients | Function | Quantity/Concentration |
|---|---|---|
| mAb | Active | 1 mg/mL |
| Sodium citrate/Citric acid | Buffer | 10 mM |
| NaCl | Isotonic agent | 9 mg/mL |
| Polysorbate 80 | Surfactant | 0.1 mg/mL |
| Water for injection | Diluent | Qs. |

TABLE 6 pH = 7 Formulation

| Ingredients | Function | Quantity/Concentration |
|---|---|---|
| mAb | Active | 1 mg/mL |
| Sodium phosphate dibasic/ Potassium phosphate monobasic | Buffer | 10 mM |
| NaCl | Isotonic agent | 9 mg/mL |
| Polysorbate 80 | Surfactant | 0.1 mg/mL |
| Water for injection | Diluent | Qs. |

TABLE 7 pH = 7.4 Formulation (PBS 1X + Polysorbate 80 0.1 mg/mL)

| Ingredients | Function | Quantity/Concentration |
|---|---|---|
| mAb | Active | 1 mg/mL |
| Sodium phosphate dibasic/ Potassium phosphate monobasic | Buffer | 10 mM |
| NaCl | Isotonic agent | 9 mg/mL |
| Polysorbate 80 | Surfactant | 0.1 mg/mL |
| Water for injection | Diluent | Qs. |

TABLE 8 pH = 8 Formulation

| Ingredients | Function | Quantity/Concentration |
|---|---|---|
| mAb | Active | 1 mg/mL |
| Sodium borate/Boric acid | Buffer | 10 mM |
| NaCl | Isotonic agent | 9 mg/mL |
| Polysorbate 80 | Surfactant | 0.1 mg/mL |
| Water for injection | Diluent | Qs. |

Initial solutions of each purified mAb were supplied in the PBS 1× formulation other formulations were obtained via buffer exchange by dialysis.

The aggregation propensity of each mAb formulation was experimentally evaluated by measurement and comparison of their aggregation temperature ($T_{agg}$). $T_{agg}$ was measured using Thermal Shift Stability Assay methodology (TSSA). TSSA measures the aggregation temperature of peptides and proteins in aqueous solutions, using the "ProteoStat Thermal Shift Stability Assay" kit (available from Enzo Life Sciences Inc., Farmingdale, N.Y.). The sample to be analyzed is heated from 0 to 100° C. and the fluorescence is read as the temperature increases. A high increase of the sample fluorescence will be detected when the aggregation temperature will be reached. This fluorescent measurement uses a 480 nm excitable molecular rotor probe. It is compatible with a wide pH range (4-10) and tolerant to surfactants such as Polysorbate 80 present at normal concentrations.

Results

Results are shown in Table 9, below. Initial purity % is measured by SE-HPLC for a PBS 1×+Polysorbate 80 at 0.1 mg/mL pH=7.4 formulation for each mAb. Runs indicated as cancelled are because their value was too far from the mean, according to study protocol. The aborted Run 1 of 2B12-H2L1 at pH 5.5 was stopped, believing that the result was aberrant as the $T_{Agg}$ value seemed very high. The result was in fact normal but not enough mAb product remained to perform a third valid run.

TABLE 9

| mAb | Theoretical pI | Initial Purity % * | pH | $T_{Agg}$ Run1 (° C.) | $T_{Agg}$ Run2 (° C.) | $T_{Agg}$ Run3 (° C.) | SD (° C.) | $T_{Agg}$ (° C.) |
|---|---|---|---|---|---|---|---|---|
| 2B12-H1L1 | 7.57 | 99.28 | 5.5 | Cancelled | 66.79 | 66.55 | 0.17 | 66.7 |
| | | | 6.5 | Cancelled | 66.49 | 66.29 | 0.14 | 66.4 |
| | | | 7 | 66.25 | 66.04 | 66.10 | 0.11 | 66.1 |
| | | | 7.4 | 66.37 | 66.13 | 66.04 | 0.17 | 66.2 |
| | | | 8 | 65.92 | 65.94 | 65.65 | 0.16 | 65.8 |
| 2B12-H1L2 | 7.57 | 99.29 | 5.5 | 66.37 | 66.35 | 66.21 | 0.09 | 66.3 |
| | | | 6.5 | 66.04 | 65.73 | 65.77 | 0.17 | 65.8 |
| | | | 7 | 65.33 | Cancelled | 65.70 | 0.26 | 65.5 |
| | | | 7.4 | 66.28 | 66.18 | 65.96 | 0.16 | 66.1 |
| | | | 8 | 65.45 | 65.73 | 65.54 | 0.14 | 65.6 |
| 2B12-H2L1 | 7.57 | 98.20 | 5.5 | Aborted | 78.80** | 79.23** | 0.30 | 79.0 |
| | | | 6.5 | 78.45 | 78.60 | 78.46 | 0.08 | 78.5 |
| | | | 7 | 79.04 | 78.67 | 78.68 | 0.21 | 78.8 |
| | | | 7.4 | 78.97 | 78.83 | 79.14 | 0.16 | 79.0 |
| | | | 8 | 78.62 | 78.41 | 78.66 | 0.13 | 78.6 |
| 2B12-H2L2 | 7.57 | 98.91 | 5.5 | 78.89 | 79.04 | 78.98 | 0.08 | 79.0 |
| | | | 6.5 | 79.04 | 78.74 | 79.17 | 0.22 | 79.0 |
| | | | 7 | 78.66 | 78.26 | 78.39 | 0.20 | 78.4 |
| | | | 7.4 | 78.75 | 78.83 | 79.00 | 0.13 | 78.9 |
| | | | 8 | 78.68 | Cancelled | 78.82 | 0.10 | 78.8 |
| 10G5-H3L2 | 8.03 | 97.65 | 5.5 | 75.37 | Cancelled | 75.75 | 0.27 | 75.6 |
| | | | 6.5 | 75.06 | 74.94 | 75.14 | 0.10 | 75.0 |
| | | | 7 | 75.40 | 75.45 | 75.62 | 0.12 | 75.5 |
| | | | 7.4 | 76.01 | 76.25 | 76.00 | 0.14 | 76.1 |
| | | | 8 | 75.71 | 75.54 | 75.61 | 0.09 | 75.6 |
| 10G5-H4L2 | 8.03 | 99.11 | 5.5 | 75.88 | 75.99 | 76.24 | 0.18 | 76.0 |
| | | | 6.5 | 76.77 | 76.54 | 76.94 | 0.20 | 76.8 |
| | | | 7 | 77.00 | 77.20 | Cancelled | 0.14 | 77.1 |
| | | | 7.4 | 76.27 | 76.54 | 76.68 | 0.21 | 76.5 |
| | | | 8 | 75.92 | 76.18 | Cancelled | 0.18 | 76.1 |

All antibodies demonstrated stability at pH values consistent with formulations that avoid chemical degradation risks of the mAbs during long term storage. Antibodies showed stability at pH=7.4 which equal to the blood pH and the chemical degradation risks of the mAb during a long term storage is lower. For all tested variants, the experimental pI values measured by gel IEF are found in the basic pH range (above pH 9). Consequently, 2B12 and 10G5 antibodies carry a net positive charge in all tested pH conditions. The selected pH conditions (pH 7.0 or 7.4) which are far below the experimental pI values will also ensure a high solubility in water for both variants.

Figure 1B:
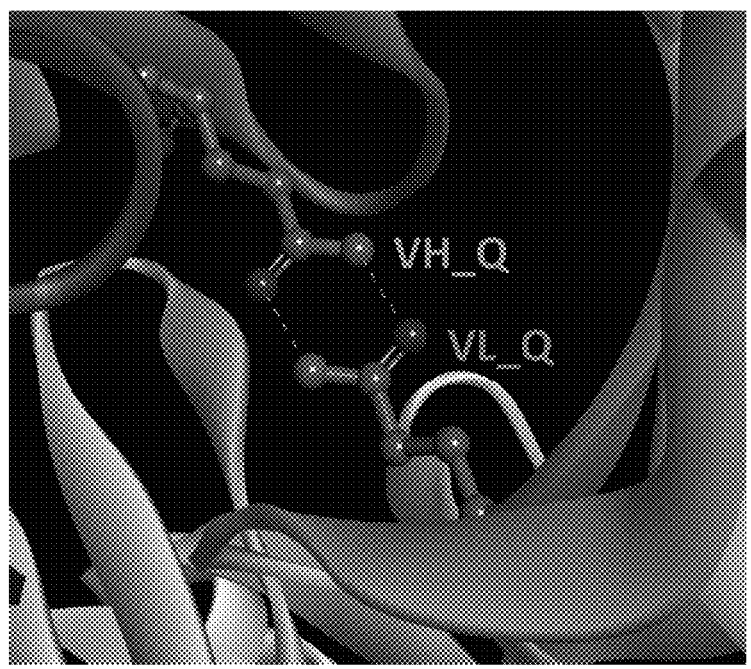

In terms of aggregation propensity, there is a surprisingly large gap between H1L1 or H1L2 and H2L1 or H2L2 variants of 2B12. H2L1 or H2L2 have a much higher aggregation temperature than H1L1 or H1L2 and thus should have a much better physical stability. This might be explained by the presence of a glutamine (Q) on H2 heavy chain in position 39 (Abnum numbering). Indeed, two H-bonds are built between VH_Q39 and VL_Q38 as shown in FIGS. 1A and 1B by the modelling of the mAb with Discovery Studio software. These two H-bonds probably stabilise the quaternary structure of the mAb, preventing exposition of certain hydrophobic areas that can be responsible for protein aggregation.

Similarly to 2B12 variants, for the H3L2 and H4L2 variants of mAb 10G5 which also have two H-bonds built between VH_Q39 and VL_Q38, high aggregation temperatures were observed. They also demonstrated good physical stability.

Example 3—Efficacy of 2B12-H2L1 Dose Response in CB17-SCID Mice Engrafted with Raji-KIR3DL2 High in IV Model The aim of this study was to assess if antibody 2B12-H2L1 could increase the life span of CB17-SCID mice intravenously (IV) engrafted with Raji-KIR3DL2 human B tumor cells, in a dose-dependent manner.

After having checked that cells expressed KIR3DL2 on their surface and bound 2B12-H2L1 antibody, 48 SCID mice were IV engrafted with 5M of Raji-KIR3DL2 high cells (Passage n° 5 and 97% of viability). IP treatments began one day after engraftment and antibodies were administered once at the dose of 0.01, 0.1, 1 µg and 10 µg/mouse.

6 groups were performed (n=8):
Control group injected with isotype control (IC) at 10 µg/mouse
Treated group injected with 2B12-H2L1 at 0.01 µg/mouse
Treated group injected with 2B12-H2L1 at 0.1 µg/mouse
Treated group injected with 2B12-H2L1 at 11 g/mouse
Treated group injected with 2B12-H2L1 at 10 µg/mouse
After IV engraftment of Raji-KIR3DL2 high cells, groups of mice treated with isotype control died quickly with a median survival of 20 days (Table 10).

Figure 2:
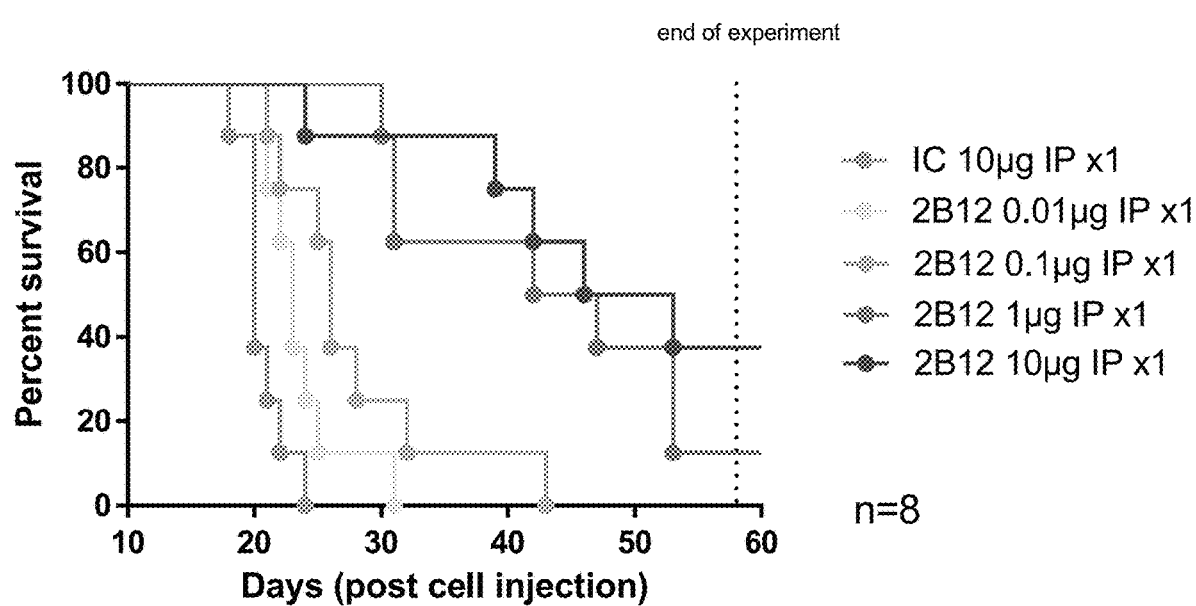
FIG. 2 shows survival curves of CB17-SCID mice engrafted with Raji-KIR3DL2 high 5M IV and treated IP with a dose response of antibody 2B12-H2L1 (n=8/group). Treatments started from day 1. End of experiment was at 58 days.

Survival curves and survival medians of groups treated with 2B12 at all doses showed a significant increase compared to control groups (FIG. 2). However, the percentage of increased life span (ILS) was much higher when mice were treated with 1 and 10 µg of mAb and none with 0.01 and 0.1 µg of mAb (Table 10). 2B12 was able to induce ADCC even at low concentrations.

Results are shown in FIG. 2. Survival curves of CB17-SCID mice engrafted with Raji-KIR3DL2 high 5M IV and treated IP with a dose response of 2B12 (n=8/group). Treatments started from day 1. End of experiment was at 58 days.

This study showed that treatment with 2B12 significantly prolonged survival of CB17-SCID mice in IV model even at low doses.

All headings and sub-headings are used herein for convenience only and should not be construed as limiting the invention in any way. Any combination of the above-described elements in all possible variations thereof is encompassed by the invention unless otherwise indicated herein or otherwise clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents. The description herein of any aspect or embodiment of the invention using terms such as reference to an element or elements is intended to provide support for a similar aspect or embodiment of the invention that "consists of," "consists essentially of" or "substantially comprises" that particular element or elements, unless otherwise stated or clearly contradicted by context (e. g. , a composition described herein as comprising a particular element

TABLE 10

|  | Isotype control 10 µg IP x1 | 2B12 0.01 µg IP x1 | 2B12 0.1 µg IP x1 | I2B12 1 µg IP x1 | 2B12 10 µg IP x1 |
|---|---|---|---|---|---|
| Median survival (days) | 20 | 23 | 26 | 44.5 | 49.5 |
| ILS (%) |  | 15 | 30 | 123 | 148 |
| Log-rank (Mantel-Cox) test |  | * (p = 0.0008) | * (p = 0.0003) | ** (p < 0.0001) | ** (p < 0.0001) | should be understood as also describing a composition consisting of that element, unless otherwise stated or clearly contradicted by context).

This invention includes all modifications and equivalents of the subject matter recited in the aspects or claims presented herein to the maximum extent permitted by applicable law.

All publications and patent applications cited in this specification are herein incorporated by reference in their entireties as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

We claim:

1. Recombinant nucleic acids encoding an antibody or antibody fragment that binds to a KIR3DL2 polypeptide, selected from the group consisting of:
   (a) an antibody or antibody fragment comprising respectively a VH and VL region comprising the amino acid sequence of SEQ ID NOS: 31 and 25,
   (b) an antibody or antibody fragment comprising respectively a VH and VL region comprising the amino acid sequence of SEQ ID NOS: 31 and 26,
   (c) an antibody or antibody fragment comprising respectively a VH and VL region comprising the amino acid sequence of SEQ ID NOS: 14 and 9, and
   (d) an antibody or antibody fragment comprising respectively a VH and VL region comprising the amino acid sequence of SEQ ID NOS: 15 and 9.

2. The nucleic acids of claim 1, wherein the antibody or antibody fragment comprises:
   (a) a heavy chain variable region comprising the amino acid sequence of SEQ ID NO: 14; and
   (b) a light chain variable region comprising the amino acid sequence of SEQ ID NO: 9.

3. The nucleic acids of claim 1, wherein the antibody or antibody fragment comprises:
   (a) a heavy chain variable region comprising the amino acid sequence of SEQ ID NO: 15; and
   (b) a light chain variable region comprising the amino acid sequence of SEQ ID NO: 9.

4. The nucleic acids of claim 1, wherein the antibody or antibody fragment comprises:
   (a) a heavy chain variable region comprising the amino acid sequence of SEQ ID NO: 31; and
   (b) a light chain variable region comprising the amino acid sequence of SEQ ID NO: 25.

5. The nucleic acids of claim 1, wherein the antibody or antibody fragment comprises:
   (a) a heavy chain variable region comprising the amino acid sequence of SEQ ID NO: 31; and
   (b) a light chain variable region comprising the amino acid sequence of SEQ ID NO: 26.

6. The nucleic acids of claim 1, wherein said antibody comprises a human heavy chain constant region comprising amino acid substitution(s) that increase binding to a human FcγIIIA (CD16) receptor.

7. A host cell comprising the nucleic acids of claim 1.

8. The host cell of claim 7, wherein the host cell is co-transfected with a vector comprising a nucleic acid encoding a variable heavy (VH) region and with a vector comprising a nucleic acid encoding a variable light (VL) region, wherein:
   a) the VH and VL region comprise the amino acid sequence of SEQ ID NOS: 31 and 25, respectively;
   (b) the VH and VL region comprise the amino acid sequence of SEQ ID NOS: 31 and 26, respectively;
   (c) the VH and VL region comprise the amino acid sequence of SEQ ID NOS: 14 and 9, respectively; or
   (d) the VH and VL region comprise the amino acid sequence of SEQ ID NOS: 15 and 9, respectively.

9. The host cell of claim 8, wherein the VH and VL regions comprise the amino acid sequence of SEQ ID NOS: 31 and 25, respectively.

10. The host cell of claim 8, wherein the VH and VL regions comprise the amino acid sequence of SEQ ID NOS: 31 and 26, respectively.

11. The host cell of claim 8, wherein the VH and VL regions comprise the amino acid sequence of SEQ ID NOS: 14 and 9, respectively.

12. The host cell of claim 8, wherein the VH and VL regions comprise the amino acid sequence of SEQ ID NOS: 15 and 9, respectively.

13. A method of producing an antibody or antibody fragment that binds to a KIR3DL2 polypeptide, the method comprising culturing host cells of claim 7 and recovering the antibody or antibody fragment from the host cell culture.

* * * * *

UNITED STATES PATENT AND TRADEMARK OFFICE
CERTIFICATE OF CORRECTION

PATENT NO. : 11,066,470 B2
APPLICATION NO. : 16/398472
DATED : July 20, 2021
INVENTOR(S) : Laurent Gauthier and Nicolas Schneider Page 1 of 1

It is certified that error appears in the above-identified patent and that said Letters Patent is hereby corrected as shown below:

In the Specification

Column 1,
Line 42, "MEW class" should read --MHC class--.

Column 2,
Line 6, "2007 J." should read --2007) J.--.

Column 7,
Line 47, "and H6" should read --and –H6--.
Line 49, "and L5;" should read --and –L5;--.

Column 14,
Line 22, "a, 6, c and g" should read --α, δ, ε and µ--.

Column 26,
Line 21, "Kd" should read --$K_d$--.
Line 22, "Kd" should read --$K_d$--.

Column 43,
Line 64, "100W" should read --100µl--.
Line 67, "100W/well" should read --100µl/well--.

Column 44,
Line 4, "(100W)" should read --(100µl)--.

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*